(12) United States Patent
Zilberstien et al.

(10) Patent No.: US 11,337,660 B2
(45) Date of Patent: May 24, 2022

(54) SAFETY MECHANISMS FOR CLOSE RANGE TOMOGRAPHIC SCANNING MACHINE AND METHODS OF USE

(71) Applicant: Spectrum Dynamics Medical Limited, Road Town (VG)

(72) Inventors: Yoel Zilberstien, Herzlia (IL); Nathaniel Roth, Tel-Aviv (IL); Idan Fogel, Natania (IL); Baha Eldeen Kassem, Mukaibla (IL)

(73) Assignee: Spectrum Dynamics Medical Limited, Road Town (VG)

( * ) Notice: Subject to any disclaimer, the term of this patent is extended or adjusted under 35 U.S.C. 154(b) by 0 days.

(21) Appl. No.: 16/756,511

(22) PCT Filed: Oct. 18, 2018

(86) PCT No.: PCT/IB2018/058094
§ 371 (c)(1),
(2) Date: Apr. 16, 2020

(87) PCT Pub. No.: WO2019/077542
PCT Pub. Date: Apr. 25, 2019

(65) Prior Publication Data
US 2020/0281546 A1 Sep. 10, 2020

Related U.S. Application Data

(60) Provisional application No. 62/574,294, filed on Oct. 19, 2017.

(51) Int. Cl.
| | | |
|---|---|---|
| *A61B 6/10* | (2006.01) | |
| *A61B 6/03* | (2006.01) | |
| *A61B 6/00* | (2006.01) | |

(52) U.S. Cl.
CPC .............. *A61B 6/102* (2013.01); *A61B 6/032* (2013.01); *A61B 6/037* (2013.01); *A61B 6/4275* (2013.01); *A61B 6/4405* (2013.01); *A61B 6/4452* (2013.01)

(58) Field of Classification Search
CPC ....... A61B 6/032; A61B 6/037; A61B 6/4725; A61B 6/4452; A61B 6/106
See application file for complete search history.

(56) References Cited

U.S. PATENT DOCUMENTS

| 3,902,070 A * | 8/1975 | Amor, Jr .............. A61B 6/4464 378/194 |
|---|---|---|
| 4,057,726 A | 11/1977 | Jaszczak |

(Continued)

FOREIGN PATENT DOCUMENTS

| WO | WO 2019/077542 | 4/2019 |
|---|---|---|
| WO | WO 2019/077542 A3 | 4/2019 |

(Continued)

OTHER PUBLICATIONS

International Preliminary Report on Patentability dated Apr. 30, 2020 From the International Bureau of WIPO Re. Application No. PCT/IB2018/058067. (6 Pages).

(Continued)

*Primary Examiner* — Carolyn A Pehlke

(57) ABSTRACT

In some embodiments, a safety system for a close range scanning machine inhibits collision of moving detector heads with a patient or other object. For example a proximity sensor and/or a collision sensor may guide to bring the head close enough to a patient and/or warn to prevent a collisions and or reduce impact. Parts that are in that are in the FOV of the detector may be transparent to the detected signal and/or uniformly affect the signal, facilitating identification of the source of the signal from the detector. In some embodiments, a dynamic motion restrictor is set during (Continued)

scanning according to the desired scanning position and/or the position of the patient. In some embodiments, a motion restrictor acts to prevent unbalanced motions.

31 Claims, 16 Drawing Sheets

(56) References Cited

U.S. PATENT DOCUMENTS

| | | | |
|---|---|---|---|
| 6,140,650 A | 10/2000 | Berlad | |
| 6,188,743 B1 | 2/2001 | Tybinkowski et al. | |
| 6,212,251 B1* | 4/2001 | Tomura | A61B 6/032 378/15 |
| 8,338,788 B2 | 12/2012 | Zilberstein et al. | |
| 8,492,725 B2 | 7/2013 | Zilberstein et al. | |
| 8,748,827 B2 | 6/2014 | Zilberstein et al. | |
| 9,606,245 B1 | 3/2017 | Czarnecki et al. | |
| 10,863,956 B2 | 12/2020 | Zilberstien et al. | |
| 2003/0209662 A1 | 11/2003 | Nelson et al. | |
| 2008/0217541 A1 | 9/2008 | Kim | |
| 2010/0061509 A1* | 3/2010 | D'Ambrosio | A61B 6/4458 378/62 |
| 2010/0188082 A1 | 7/2010 | Morich et al. | |
| 2011/0103544 A1 | 5/2011 | Hermony | |
| 2015/0028218 A1 | 1/2015 | Kataoka et al. | |
| 2015/0065874 A1 | 3/2015 | Rafaeli et al. | |
| 2015/0094571 A1 | 4/2015 | Bouhnik et al. | |
| 2015/0119704 A1 | 4/2015 | Roth et al. | |
| 2015/0276949 A1 | 10/2015 | Grobshtein et al. | |
| 2015/0342543 A1 | 12/2015 | Khen et al. | |
| 2016/0007941 A1 | 1/2016 | Hefetz | |
| 2016/0313263 A1 | 10/2016 | Featonby et al. | |
| 2016/0380728 A1 | 12/2016 | Dudek et al. | |
| 2017/0014096 A1 | 1/2017 | Bouhnik et al. | |
| 2017/0082759 A1 | 3/2017 | Lyu et al. | |
| 2017/0112454 A1 | 4/2017 | Yun et al. | |
| 2017/0153338 A1 | 6/2017 | Kovalski et al. | |
| 2017/0189720 A1 | 7/2017 | Liu et al. | |
| 2017/0332025 A1 | 11/2017 | Nozawa et al. | |
| 2018/0059270 A1 | 3/2018 | Hefetz et al. | |
| 2018/0110496 A1 | 4/2018 | Levy et al. | |
| 2020/0163631 A1* | 5/2020 | Okuno | A61B 6/102 |
| 2020/0289074 A1 | 9/2020 | Zilberstien et al. | |
| 2020/0297296 A1 | 9/2020 | Zilberstien et al. | |
| 2020/0301033 A1 | 9/2020 | Roth et al. | |
| 2021/0093270 A1 | 4/2021 | Zilberstien et al. | |

FOREIGN PATENT DOCUMENTS

| | | |
|---|---|---|
| WO | WO 2019/077544 | 4/2019 |
| WO | WO 2019/077548 | 4/2019 |
| WO | WO 2019/077548 A3 | 4/2019 |
| WO | WO 2019/077552 | 4/2019 |

OTHER PUBLICATIONS

International Preliminary Report on Patentability dated Apr. 30, 2020 From the International Bureau of WIPO Re. Application No. PCT/IB2018/058094. (7 Pages).
International Preliminary Report on Patentability dated Apr. 30, 2020 From the International Bureau of WIPO Re. Application No. PCT/IB2018/058102. (8 Pages).
International Preliminary Report on Patentability dated Apr. 30, 2020 From the International Bureau of WIPO Rc. Application No. PCT/IB2018/058108. (10 Pages).
International Search Report and the Written Opinion dated Apr. 23, 2019 From the International Searching Authority Re. Application No. PCT/IB2018/058108. (20 Pages).
International Search Report and the Written Opinion dated Apr. 24, 2019 From the International Searching Authority Re. Application No. PCT/IB2018/058094. (15 Pages).
International Search Report and the Written Opinion dated Apr. 24, 2019 From the International Searching Authority Re. Application No. PCT/IB2018/058102. (16 Pages).
International Search Report and the Written Opinion dated Feb. 25, 2019 From the International Searching Authority Re. Application No. PCT/IB2018/058067. (12 Pages).
Invitation to Pay Additional Fees dated Feb. 7, 2019 From the International Searching Authority Re. Application No. PCT/IB2018/058094. (2 Pages).
Invitation to Pay Additional Fees dated Feb. 7, 2019 From the International Searching Authority Re. Application No. PCT/IB2018/058102. (3 Pages).
Invitation to Pay Additional Fees dated Feb. 7, 2019 From the International Searching Authority Re. Application No. PCT/IB2018/058108. (2 Pages).
Notice of Allowance dated Aug. 12, 2020 from the US Patent and Trademark Office Re. U.S. Appl. No. 16/756,492. (9 pages).
Interview Summary dated Mar. 19, 2021 From the US Patent and Trademark Office Re. U.S. Appl. No. 16/756,496. (2 Pages).
Official Action dated Sep. 9, 2020 from the US Patent and Trademark Office Re. U.S. Appl. No. 16/756,496. (27 pages).
Final Official Action dated Feb. 23, 2021 From the US Patent and Trademark Office Re. U.S. Appl. No. 16/756,496. (25 Pages).
Supplementary European Search Report and the European Search Opinion dated Jun. 9, 2021 From the European Patent Office Re. Application No. 18868387.4. (7 Pages).
Supplementary European Search Report and the European Search Opinion dated Jun. 21, 2021 From the European Patent Office Re. Application No. 18869300.6. (8 Pages).
Official Action dated Jul. 7, 2021 from the US Patent and Trademark Office Re. U.S. Appl. No. 16/756,496. (12 pages).
Supplementary European Search Report and the European Search Opinion dated Jul. 14, 2021 From the European Patent Office Re. Application No. 18869177.8. (8 Pages).
Supplementary European Search Report and the European Search Opinion dated Jun. 4, 2021 From the European Patent Office Re. Application No. 18868897.2. (7 Pages).

* cited by examiner

SAFETY MECHANISMS FOR CLOSE RANGE TOMOGRAPHIC SCANNING MACHINE AND METHODS OF USE

RELATED APPLICATIONS

This application is a National Phase of PCT Patent Application No. PCT/IB2018/058094 having International filing date of Oct. 18, 2018, which claims the benefit of priority under 35 USC § 119(e) of U.S. Provisional Patent Application No. 62/574,294 filed on Oct. 19, 2017. The contents of the above applications are all incorporated by reference as if fully set forth herein in their entirety.

PCT Patent Application No. PCT/IB2018/058094 is also related to co-filed, and co-assigned:

International Patent Application No. PCT/IB2018/058102 filed on Oct. 18, 2018 entitled "COOLING OF A NUCLEAR MEDICINE TOMOGRAPHY SYSTEM" which claims the benefit of priority of U.S. Provisional Patent Application No. 62/574,345 filed on Oct. 19, 2017.

International Patent Application No. PCT/IB2018/058108 filed on Oct. 18, 2018 entitled "CALIBRATION AND QUALITY CONTROL OF A NUCLEAR-MEDICINE (N-M) RADIO IMAGING SYSTEM" which claims the benefit of priority of U.S. Provisional Patent Application No. 62/574,300 filed on Oct. 19, 2017.

International Patent Application No. PCT/IB2018/058097 filed on Oct. 18, 2018 entitled "MOVING PARTS IN A NUCLEAR MEDICINE (N-M) IMAGING SYSTEM" which claims the benefit of priority of U.S. Provisional Patent Application No. 62/574,277 filed on Oct. 19, 2017, and the contents of which are all incorporated by reference as if fully set forth herein in their entirety.

PCT Patent Application No. PCT/IB2018/058094 is also related to U.S. patent application Ser. No. 14/399,975, U.S. Pat. Nos. 8,338,788, 8,492,725 and 8,748,827, the contents of which are all incorporated by reference as if fully set forth herein in their entirety.

FIELD AND BACKGROUND OF THE INVENTION

The present invention, in some embodiments thereof, relates to safety features of a close range tomographic scanning machine and, more particularly, but not exclusively, to safely positioning scanning heads near a patient.

U.S. Pat. No. 8,338,788 to the present inventors and others appears to disclose "A system of performing a volumetric scan. The system comprises a surface of positioning a patient in a space parallel thereto, a plurality of extendable detector arms each the detector arm having a detection unit having at least one radiation detector, and an actuator which moves the detection unit along a linear path, and a gantry which supports the plurality of extendable detector arms around the surface so that each the linear path of each respective the extendable detector arm being directed toward the space."

U.S. Patent Application Publication No. 2010/0061509 entitled Detector Head Proximity Sensing and Collision Avoidance Apparatuses and Methods appears to disclose, "A gamma camera (8, 180) includes at least one radiation detector head (10, 12, 210, 212). At least one such radiation detector head (10, 12, 210, 212) includes a plurality of capacitive elements (60, 260, 76, 276) disposed over at least a radiation sensitive portion (50) of the radiation detector head. A proximity sensor monitor (62) is coupled with the plurality of capacitive elements to detect proximity of a subject to the radiation detector head based on a measured electrical characteristic of the capacitive elements. A collision sensor monitor (64) is coupled with the plurality of capacitive elements to detect conductive electric current flowing between spaced apart parallel conductive plates (66, 67) of the capacitive element responsive to mechanical deformation of the spacing between the plates."

U.S. Patent Application Publication No. 2015/0119704 to the instant inventors and others appears to disclose, "An N-M tomography system comprising: a carrier for the subject of an examination procedure; a plurality of detector heads; a carrier for the detector heads; and a detector positioning arrangement operable to position the detector heads during performance of a scan without interference or collision between adjacent detector heads to establish a variable bore size and configuration for the examination. Additionally, collimated detectors providing variable spatial resolution for SPECT imaging and which can also be used for PET imaging, whereby one set of detectors can be selectably used for either modality, or for both simultaneously."

SUMMARY OF THE INVENTION

According to an aspect of some embodiments of the invention, there is provided a tomographic system including: a support for a subject in an examination procedure at least one detector head; a mobile carrier translating along an axially along the support and pivoting circumferentially around the support; an extender supporting the detector head on the carrier and dynamically positioning the detector head along a path between the support and the carrier before and/or during performance of a scan to establish a variable bore size and configuration for the examination; a counter weight for the detector head, the counter weight balancing a force of gravity of the detector head along the path; a restrictor limiting movement of the extender in response to an unbalanced movement of the head with respect to the counter weight.

According to some embodiments of the invention, the system further includes: a belt connecting between the detection head and the counterweight; a sensor responsive to a malfunction of the belt to trigger the restrictor.

According to some embodiments of the invention, the restrictor includes a brake inhibiting movement of the detector towards the support.

According to some embodiments of the invention, the system further includes at least two rollers guiding the belt; and wherein the sensor includes a cord connected between the at least two rollers, and wherein the response of the sensor includes a change in tension of the cord in response to an uncoordinated rotation of the at least two rollers.

According to an aspect of some embodiments of the invention, there is provided a tomographic system including: a support for a subject in an examination procedure at least one detector head; a mobile carrier supporting the detector head; the mobile carrier translating along an axially along the support and pivoting circumferentially around the support; an actuator, coupled to the detector head to dynamically extend the detector head toward the support before and/or during performance of a scan to establish a variable bore size and configuration for the examination; a passive biasing member 350 retracting the detection head away from the support toward the carrier.

According to some embodiments of the invention, the biasing member includes an elastic member.

According to an aspect of some embodiments of the invention, there is provided a method of protecting a patient from impact from a scanning head of a tomography system that includes a support for a subject of a tomography procedure and a detector arrangement comprised of plurality of detector heads that are adjustably positionable on a detector carrier the method including: selecting a bore geometry for the detector array according to a particular region of interest of a subject of a procedure by extending and rotating about a pivot one or more detector heads such that adjacent detector heads do not interfere with each other; defining a limit position of the at least one head; setting a restrictor limiting movement of the detector head in response to the detector head reaching the limit position.

According to some embodiments of the invention, the tomography system includes a plurality of indicator switches, each indicator switch indicating a different location of the detection head and wherein the setting includes: selecting critical switch of the plurality of switches indicating that the head has reached the limit position; and linking the critical switch to a movement restrictor.

According to some embodiments of the invention, the linking includes: setting a watchdog on the critical indicator switch to stop at least one of the rotating and the extending of the at least one detector head when the critical switch indicates that the at least one head has reached the limit position.

According to some embodiments of the invention, the tomography system includes a plurality of movement blocking stops, each stop blocking movement at a different location of the detection head and wherein the setting includes: selecting critical stop of the plurality of stops; and activating the critical stop to block at least one of the rotating and the extending of the at least one detector head past the limit position.

According to an aspect of some embodiments of the invention, there is provided a tomographic system including: a support for a subject in an examination procedure at least one detector head having a field of view including a plurality of directions; a mobile carrier supporting the detector head; the mobile carrier translating along an axially along the support and pivoting circumferentially around the support; an actuator, coupled to the detector head for extending the detector head toward the support before and/or during performance of a scan to establish a variable bore size and configuration for the examination; a shield positioned between the detector head and the support, the shield configured to attenuate a signal detected by the detector uniformly over the field of view; a force sensor detecting a force on the shield, the force detector positioned outside the field of view.

According to some embodiments of the invention, the shield is transparent to a signal detected by the detector.

According to some embodiments of the invention, the system further includes a support connected the shield to a detector head and wherein the force sensor detects a strain on the support.

According to some embodiments of the invention, the actuator is in communication with the sensor to stop the extending in response to a signal from the sensor.

According to some embodiments of the invention, the actuator is in communication with the sensor to reverse the extending in response to a signal from the sensor.

According to an aspect of some embodiments of the invention, there is provided a tomographic system including: a support for a subject in an examination procedure at least one detector head having a field of view including a plurality of directions; a mobile carrier supporting the detector head; the mobile carrier translating along an axially along the support and pivoting circumferentially around the support; an actuator, coupled to the detector head to dynamically extend the detector head toward the support before and/or during performance of a scan to establish a variable bore size and configuration for the examination; a capacitance detector positioned between the detector head and the support, the capacitance detector configured to attenuate a signal detected by the detector uniformly over the field of view.

According to some embodiments of the invention, the capacitance detector includes: a conductive layer configured to uniformly attenuate a signal detected by the detector over the field of view; and a plurality of insulators defining a plurality of isolated islands in the conductive layers, each island detecting capacitance is a different portion of the field of view.

According to some embodiments of the invention, the conductive layer is homogeneous over at least 95% of the field of view.

According to some embodiments of the invention, the capacitance detector includes an insulating layer supporting the conductive layer.

According to some embodiments of the invention, the system further includes: a sensing circuit, sensitive to a charge on at least one of the islands; the sensing circuit located outside of the field of view of the detection head.

According to some embodiments of the invention, the actuator is in communication with the sensor circuit to stop the extending in response to a signal from the sensor circuit.

According to an aspect of some embodiments of the invention there is provided a tomographic system comprising: a support for a subject in an examination procedure at least one detector head; a mobile carrier configured to rotate around said support; an extender supporting said detector head on said carrier and dynamically positioning said detector head along a path between said support and said carrier before and/or during performance of a scan; a counter weight for said detector head, said counter weight balancing a force of gravity of said detector head along said path; a restrictor limiting movement of said extender in response to an unbalanced movement of said head with respect to said counter weight.

According to some embodiments of the invention said system includes: a belt connecting between said detection head and said counterweight; at least one sensor responsive to a malfunction of said belt to trigger said restrictor.

According to some embodiments of the invention said malfunction includes a loss of tension in said belt.

According to some embodiments of the invention said system comprises at least two rollers guiding said belt; wherein said sensor includes a cord connected between said at least two rollers, and wherein said at least one sensor measures a change in tension in said cord in response to an uncoordinated rotation of said at least two rollers.

According to some embodiments of the invention said at least two rollers are biased to rotate in opposite directions, reduction in tension of said belt thereby increasing tension on said cord.

According to some embodiments of the invention said restrictor includes a brake configured to inhibit movement of said detector towards said support.

According to some embodiments of the invention said system comprises a brake including an actuator configured to activate the brake, said system comprising: a controller receiving a signal from said at least one sensor, said controller including circuity configured to generate a control signal for control of said brake, based on said signal.

According to some embodiments of the invention said sensor is configured to measure and said controller is configured to generate a control signal based on one or more of: tension on one or more of said cord and said belt; and speed of movement of said detector head.

According to some embodiments of the invention said restrictor includes a brake configured to inhibit movement of said detector towards said support; wherein said brake is activated upon a change in tension on said cord.

According to some embodiments of the invention wherein said restrictor includes a brake configured to inhibit movement of said detector towards said support; wherein said brake is activated upon a change in tension on said belt.

According to some embodiments of the invention, said system comprises a controller receiving signals from said sensor and including circuitry configured to alert a user upon said malfunction in said belt.

According to some embodiments of the invention said system comprises a passive biasing member configured to retract said detection head away from said support and towards said carrier.

According to some embodiments of the invention said passive biasing member comprises an elastic member.

According to an aspect of some embodiments of the invention there is provided a nuclear medicine (NM) tomography system comprising: a carrier; a low voltage power source;

a plurality of detector units, each unit comprising: a detector array; and a power converter electrically connected to said low voltage power source and to said detector array and configured to step up said low voltage power source and provide high voltage power to said detector array.

According to some embodiments of the invention said carrier comprises a bore; and wherein each said detector unit is mounted on said carrier and configured to extend, into said bore. According to some embodiments of the invention said each detector array is a cadmium zinc telluride detector array. According to some embodiments of the invention said low voltage is lower than 50V. According to some embodiments of the invention said high voltage is higher than 300V.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

DESCRIPTION OF SPECIFIC EMBODIMENTS OF THE INVENTION

Figure 1:
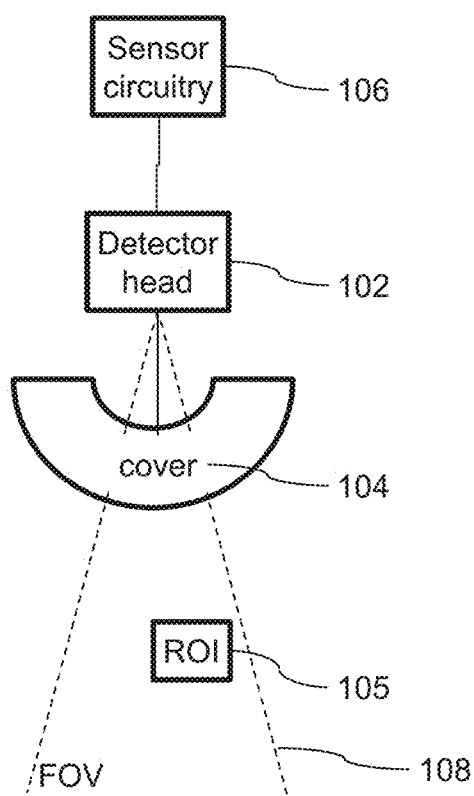
FIG. 1 is a schematic illustration of a system for sensing a collision in accordance with an embodiment of the current invention.

The present invention, in some embodiments thereof, relates to safety features of a close range tomographic scanning machine and, more particularly, but not exclusively, to safely positioning scanning heads near a patient.

Overview

In some embodiments of the current invention, safety features are supplied for a close range tomographic scanning machine e.g. a nuclear medicine tomographic scanning machine (e.g. a SPECT imaging machine). In some embodiments, a close range tomographic scanning machine includes one or more mobile detection heads. A detection head may be positioned by extending towards a patient, rotating around a patient and/or translating along the patient. Movement of the detection head along contours of the patient's body and/or movements of the patient and/or extension of the detection head towards the patient carry a danger that the scanning head may collide with and/or hurt the patient. Other hazards may include electrical shock and/or trapping of the patient by the machine.

A broad aspect of some of embodiments of the invention relates to a system with multiple safety features. Where, for example, movement of one or more detector head is monitored and/or restricted and/or controlled using a plurality of safety mechanisms. For example, a detector head (e.g. each detector head), in some embodiments, includes a plurality features selected from those described within this document. For example, one or more safety feature selected from: one or more restrictor, one or more proximity detector, one or more balancing mechanism and one or more passive return mechanism.

For example, in some embodiments, a restrictor prevents uncontrolled movement of a detector head e.g. associated with malfunction (e.g. mechanical and/or software) and/or during calibration and/or bore size selection and/or large movements of the detector head. Then, in some embodiments, in addition, smaller movement/s are controlled using proximity detection.

In some embodiments, a system includes proximity detector/s and collision/contact detector/s where, for example, failing correct positioning (e.g. prevention of collision) of detector head/s using proximity detectors, a force of impact of detector head/s is reduced (e.g. with a patient and/or with other system component/s e.g. another detector head).

An aspect of some embodiments of the current invention relates to a movement restrictor for a detection head of a close range tomographic scanning machine. In some embodiments the weight of a detection head is balanced, for example by a counter weight. Optionally, a safety mechanism restricts movement/s of the detection head that are not coordinated with movement of the balancing mechanism.

In some embodiments, a linkage may connect the detection head to the balancing mechanism. Should the linkage fail, the unbalanced weight of the detection head may cause uncontrolled movements and/or a collision with a patient. Optionally, uncoordinated movement between the detection head and/or the balancing mechanism may activate a movement restrictor. For example, the restrictor may impede extension of the detection head toward the patient.

In some embodiments, a balancing mechanism may be configured to soften movement of a heavy detector head. For example, the balancing may allow movement of a detector head with a low power motor and/or a low force. For example, this may avoid high force collisions with the patient. Alternatively or additionally, a balancing mechanism may be designed to enable a patient and/or an aide to manually push a detector head. For example, a head may be pushed away from a collision course with the patient and/or a head may be pushed away to clear the patient from the machine. Optionally, the balancing mechanism is designed to balance movement of the detector head independent of the angle at which the head is positioned. For example, a counter weight may be positioned on an extender moving opposite the detector head. Optionally, when an angle of the extender changes, the angle of the weight also changes accordingly.

In some embodiments, a counter balance may be used for a rotation motion. For example, when a detector head is directed on a horizontal radius of the gantry, outward radial movement of the detector head will cause an increased torque on the gantry. As the detector moves outward, a counterweight moves inward reducing the torque on the gantry and preserving the rotational balance of the gantry. Optionally, the weights and/or movement rates of various balancing components are designed to keep the gantry rotationally balanced. The rotational weight balance of the gantry may prevent spontaneous rotation of the gantry in case of a control system failure (for example an electrical failures). Such spontaneous rotation could endanger a patient. Other balancing weights may optionally be supplied to rotationally balance the system.

An aspect of some embodiments of the current invention relates to a safety return for a detector head. In some cases a malfunction (for example a loss of electrical power) would leave a patient trapped by one or more detection heads. Optionally, a passive return mechanism retracts a detection head away from a patient upon failure of the head positioning system.

In some embodiments, a detection head may be biased away from a patient. For example, the biasing may be due to a passive force counter weight and/or due to an elastic element (e.g. a spring and/or an elastic band). In some embodiments, movement of the head towards the patient may be performed using an active control system. Failure of the active control system may cause return of the detection head to its biased position, retracted away from the patient.

An aspect of some embodiments of the current invention relates to adjustable restrictors for a detection head of a close range scanning machine. In some embodiments, a before moving a scanning head, a limiting position of the detector head is defined. and/or an adjustable restrictor is set to block movement of the detection head past the limiting position.

In some embodiments, a safety restrictor may include a physical movement blocker. For example, a detection head may be mounted to an arm that extends toward a patient. The arm may include multiple retractable stops. When a stop is retracted it optionally does not block movement of the scan head. When the stop is extended it optionally blocks movement of the scan head. For example, once a safety limit for movement is set, a restrictor at a position before the limiting position is activated (e.g. extended) preventing movement of the detector head towards the patient beyond the limiting position.

In some embodiments, a safety restrictor may include an indicator switch. For example, there may be a plurality of switches, each switch indicating a position of the detection head. Optionally, a critical switch is identified. For example, the critical switch may indicate that the detector head has reached the limiting position. A watchdog may be activated that will restrict movement of the detector head when a critical switch is triggered. Optionally, a set of critical switches may be identified and/or a multistage watchdog may be set dependent on multiple switches and/or conditions.

An aspect of some embodiments of the current invention relates to configuring a proximity sensor to sense proximity of a patient and/or another object to a detection head while reducing interference to detection of a condition being measured. For example, a proximity sensor may be designed with components outside of the field of view FOV of the detection head. Alternatively or additionally, the components of the proximity sensor that are located in the FOV of the detection head may be designed to affect the detected signal in a uniform and/or well characterized way such that the signal can be reconstructed accurately. For example, there may be no wires and/or electronic element in the FOV of the detection head. Optionally, the proximity sensor is shaped to facilitate close and/or even approach of the detection head to a ROI (region of interest). For example, the shape of the proximity sensor may be contoured to the scanning path of the detection head and/or facilitate approach of the detection head to the patient at the same distance from different angles.

Figure 16:
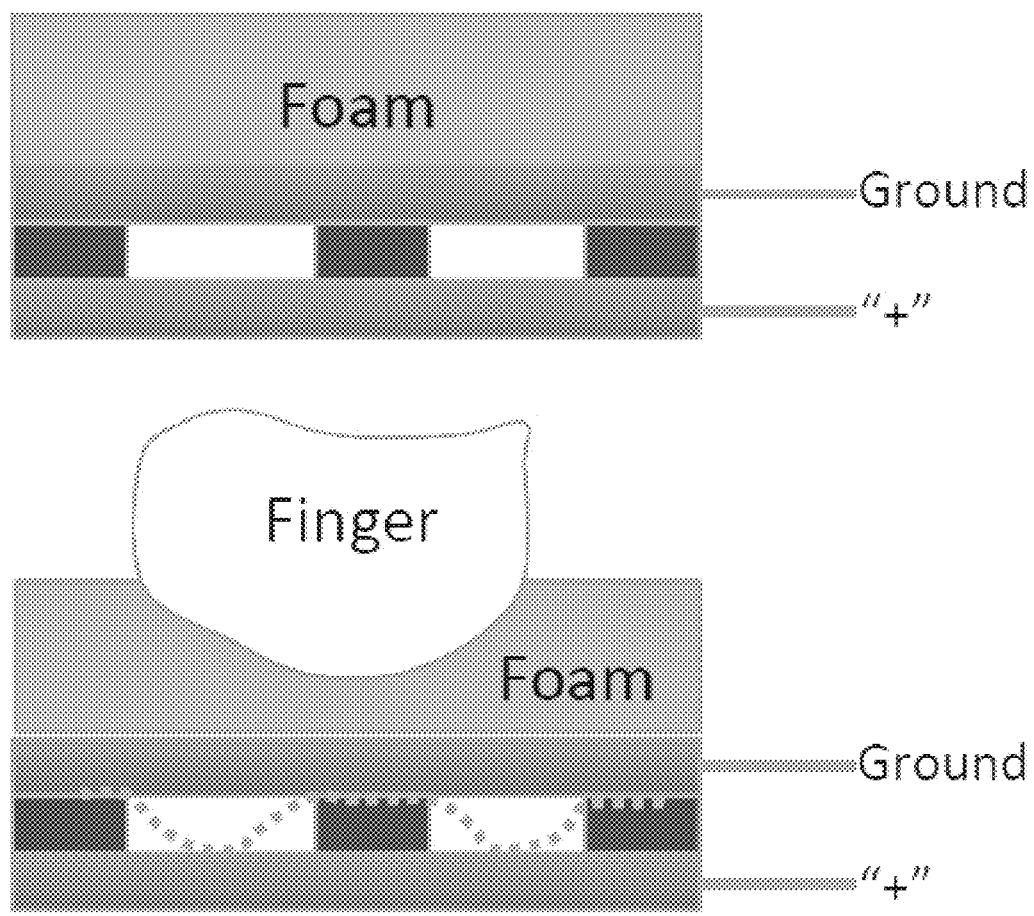
FIG. 16 is a schematic illustration of a collision detector in accordance with an embodiment of the current invention.

In some embodiments a proximity sensor may include a contact sensor e.g. including one or more feature as described regarding and/or illustrated in FIG. 16. For example, a contact sensor may include a pressure sensitive surface located between the detection head and the patient (for example in the FOV of the detection head). For example, the pressure sensitive surface may be designed of one or more homogeneous conductive layers. The conductive layers may be separated by insulating sections. The insulating material is optionally relatively transparent to the measured signal. Optionally pressure causes a contact between the conductive layers which can be measured by a sensor circuit. Optionally the sensor circuit is located outside the FOV of the detection head.

In some embodiments, a collision sensor may include a shield that is fit to the detection head. For example a portion of the shield that is in the field of view of the detection head may composed of a material that is transparent to the measured signal and/or interferes evenly with the signal over the FOV of the detection head. Optionally, a sensor circuit is connected to the shield and/or to a support of the shield. For example, the detection circuit and/or the support may be positioned out of the FOV of the detection head. Collision between the shield and an object (for example a patient) optionally causes stress that is measured by the sensor circuit.

In some embodiments, a proximity sensor may include a capacitance sensor. For example a capacitance sensor may include one or more conductive layers that have homogeneous and/or well characterized interference with the measured signal over the FOV of the detection head (for example a thin almost continuous sheet of a homogenous conductor for example Copper). Optionally, the conductor is divided into islands. For example small portions of the conducting layer may be cut out and/or interrupted by an insulator. For example, the conducting layer may be supported on the insulating layer with thin breaks in the conducting layer forming the islands. Optionally the insulating layer is transparent to the detected signal and/or uniformly affects the signal (for example the insulator may be made of ABS and/or PVC and/or silicone). Optionally connecting lines are cut into the Copper sheet and/or formed on an opposite face of the insulating sheet. For example, a second Copper sheet may cover an opposite side of the insulating sheet, the second Copper sheet being cut out to form connectors. Optionally, capacitance at each island is measured by a sensor circuit outside the FOV of the detection head. For example, the sensing circuit may be connected to the islands by means of the connecting lines. Optionally, when an island approaches an object, the object induces a charge on the island which is sensed by the sensing circuit. Optionally, the capacitance sensor may be flexible and/or take a form that is fit to the scanning path of the detector head.

In some embodiments, proximity sensor may include a strain gauge, a capacitance sensor, resistive sensor, an ultrasound ranging sensor, a laser ranging sensor, a magnetic sensor. Optionally, parts of the proximity sensor that may interfere with a detected signal are kept out of the FOV of the detector.

An aspect of some embodiments of the current invention relates to an enhanced safety power supply for a detection head. In some embodiments, a detection head may require a high current high voltage power supply. Especially for a device with multiple detection heads, the electrical power supply to the heads include voltage and current high enough to injure a patient if the patient is accidently exposed to an electric power cable. In some embodiments of the current invention the power cable of a tomographic scanning machine will carry an electrical signal with reduced danger (for example a low voltage high current signal) and a voltage converter will be supplied near the detection head that will convert the electrical power to a form fitting to power the detection head. For example, a cable may connect a low voltage supply, for example, a 1-50V, or a 10-50V, or a 10-100V, or a less than 100V or a less than 50V or a less than 30V, or an about 24V, or lower or higher or intermediate voltage power supplies to the detection head. At the detection head, the power may be converted to high voltage e.g. 600V (e.g. between 300 to 1000V, between 300 and 2000V, or between 500 and 600V, or over 300V or over 500V or lower or higher or intermediate ranges or voltages) for use in detection. Alternatively or additionally, high current power cables (supplying multiple detectors heads) may run at low voltage and/or low current cables (for example powering a single head) may carry high voltage. In some embodiments, localizing dangerous voltages and/or avoid high voltage on cables carrying high power may prevent electrocution of a patient.

In an exemplary embodiment, a low voltage power supply is supplied to each of a plurality of detection heads. In some embodiments, for one or more detector head, e.g. for each detector head, the power supply is stepped up to a high voltage e.g. a voltage high enough for operation of semiconductor radiation sensor/s e.g. a CZT detector array.

Potentially, additional complexity of having each detector head include a power convertor increase risk of overall system malfunction (risk of malfunction of a plurality of power convertors as opposed to a single converter).

In some embodiments, the imaging system is a modular system capable of operating with a variable number of detector heads, for example, where a detector head is added to and/or removed from the system. For example, where the system is capable of operating (e.g. scanning tissue) when one or more of the detector heads is deactivated (e.g. due to malfunction).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Embodiments

Referring now to the drawings, FIG. 1 is a schematic illustration of a detection head with a sensor to protect a patient from collisions in accordance with an embodiment of the current invention. In some embodiments, a shield 104 is located between a detection head 102 and a region of interest 105. Optionally the shield 104 is composed of a material that uniformly affects the signal being detected (for example collision shield 104 may uniformly attenuate a signal and/or shield 104 may be substantially transparent to the signal). In some embodiments, components that may have a complex effect on the measured signal, for example sensor circuitry 106 are positioned outside of the FOV 108 of detector head 102. For example, the signal arriving at detector 102 an easily be reconstructed to determine the strength and location of the signal from the ROI.

Optionally, shield 104 uniformly covers the FOV 108 of detection head 102. Alternatively or additionally, shield 104 is uniformly distanced from the detection head 102 and/or allows the detection head 102 to approach ROI 105 from different directions.

In some embodiments, shield 104 includes a charge collecting plate (for example flexible capacitance board 530, 830, 930 and/or 1039 as illustrated for example in FIGS. 5, 7, 8, 9A-B, and/or 10). In some embodiments, sensor circuitry 106 includes capacitance based proximity detection circuitry (for example circuit 840 as illustrated for example in FIG. 8).

Figure 5:
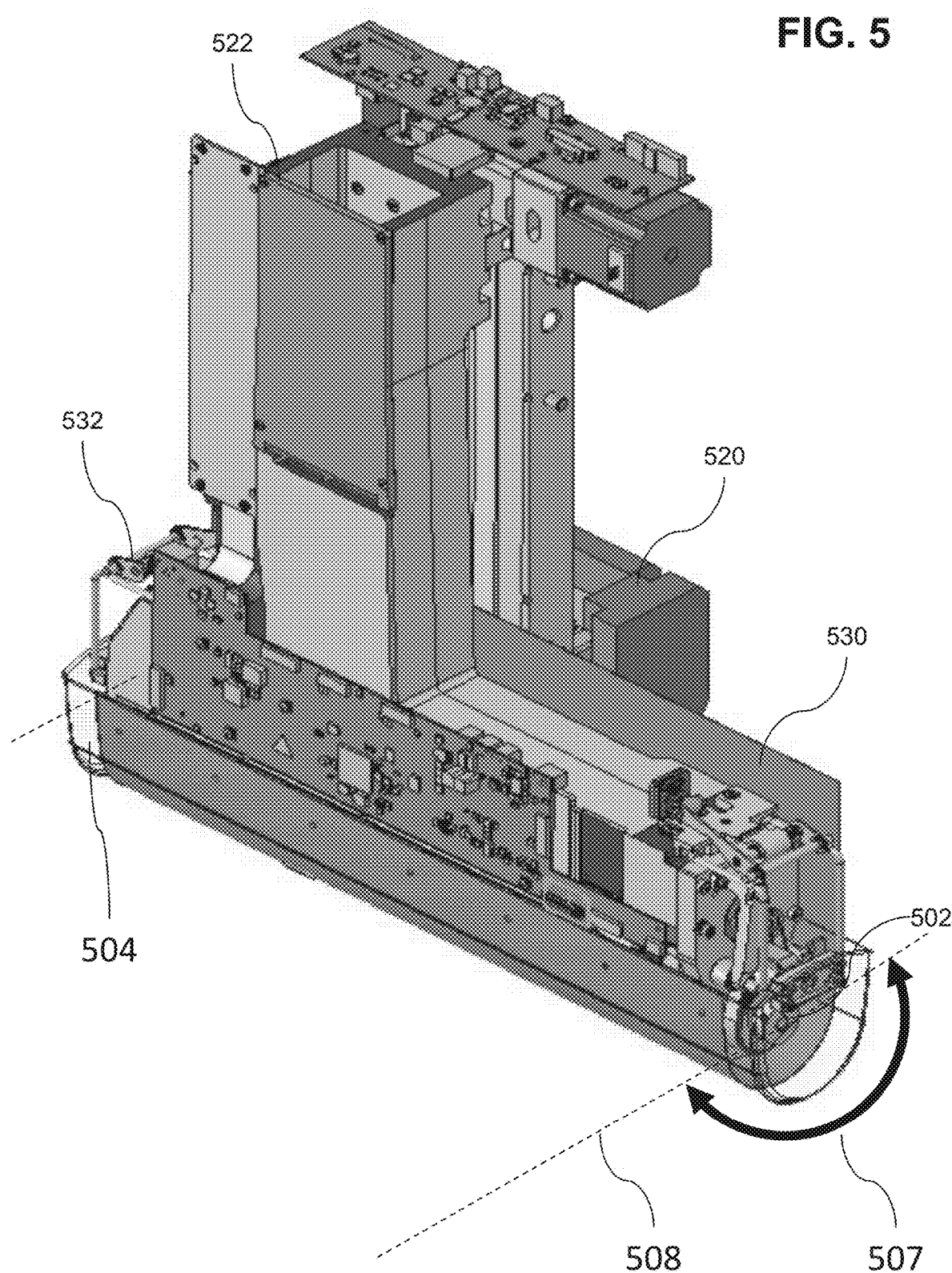
FIG. 5 is a perspective drawing of a detection head, an extension arm, a proximity sensor and a collision sensor in accordance with an embodiment of the current invention.
Figure 6:
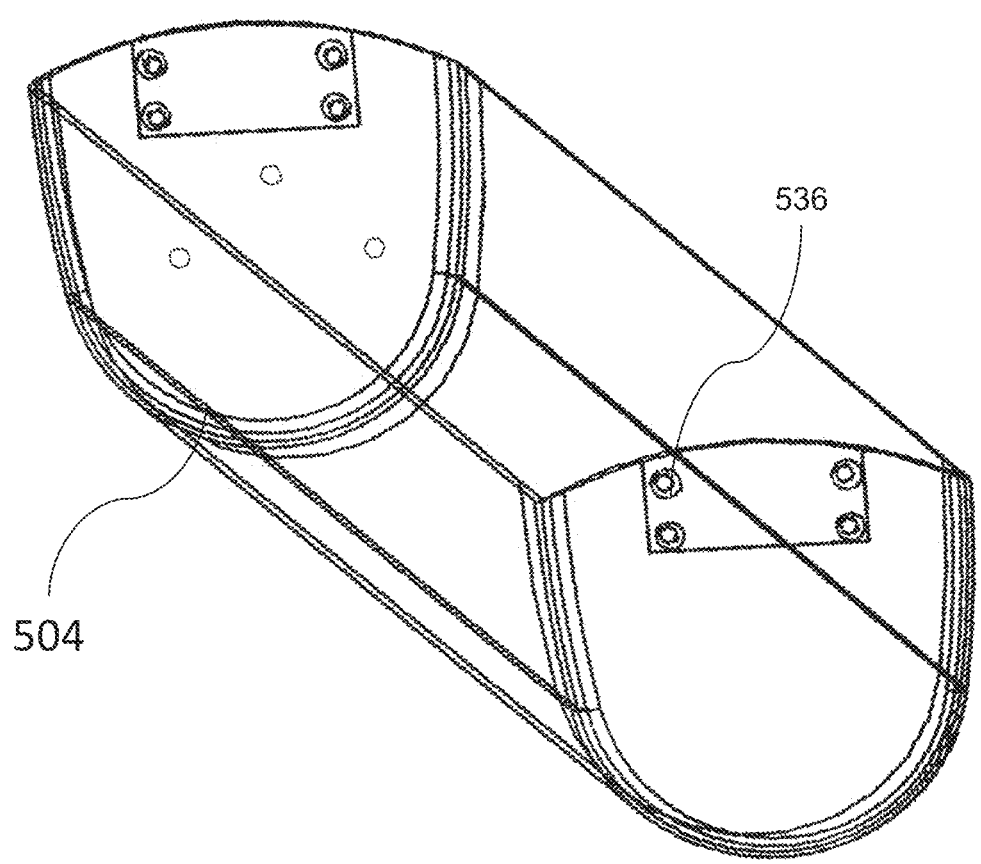
FIG. 6 is a is a perspective drawing of a collision sensor shield in accordance with an embodiment of the current invention.
Figure 7:
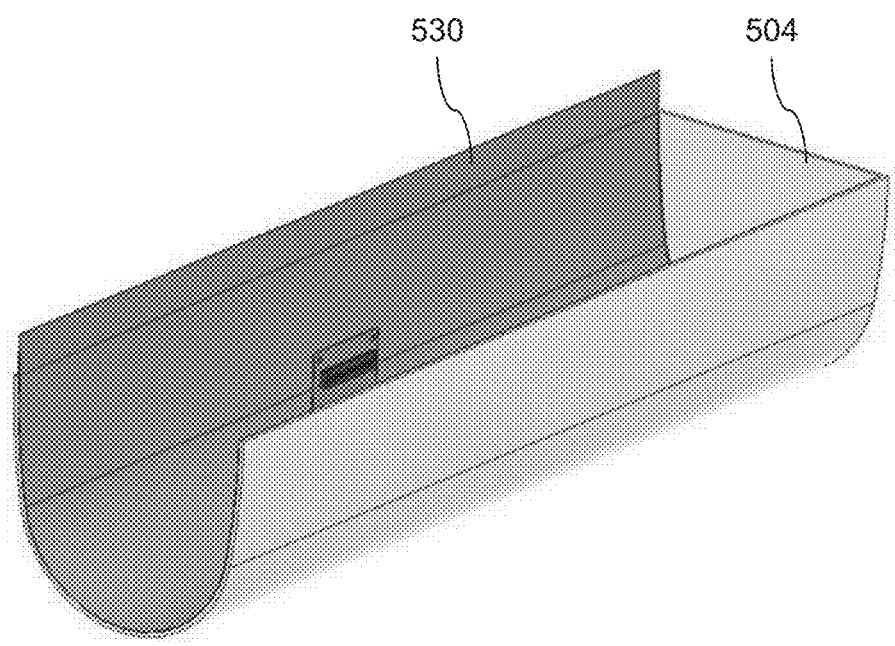
FIG. 7 is a perspective drawing of a proximity sensor and a collision sensor shield in accordance with an embodiment of the current invention.

In some embodiments, shield 104 includes a passive shield (for example shields 504 and/or 1104 as illustrated for example in FIGS. 5, 6, 7, and/or 11). In some embodiments, sensor circuitry 106 includes a support structure (for example supports 532 and/or 1132 illustrated for example in FIGS. 5 and/or 11). In some embodiments, sensor circuitry 106 includes a stress and/or movement sensor (for example sensor 1106 illustrated for example in FIG. 11).

In some embodiments, shield 104 may include a touch sensitive structure, for example the touch sensitive foam structure illustrated in FIG. 16.

Figure 2:
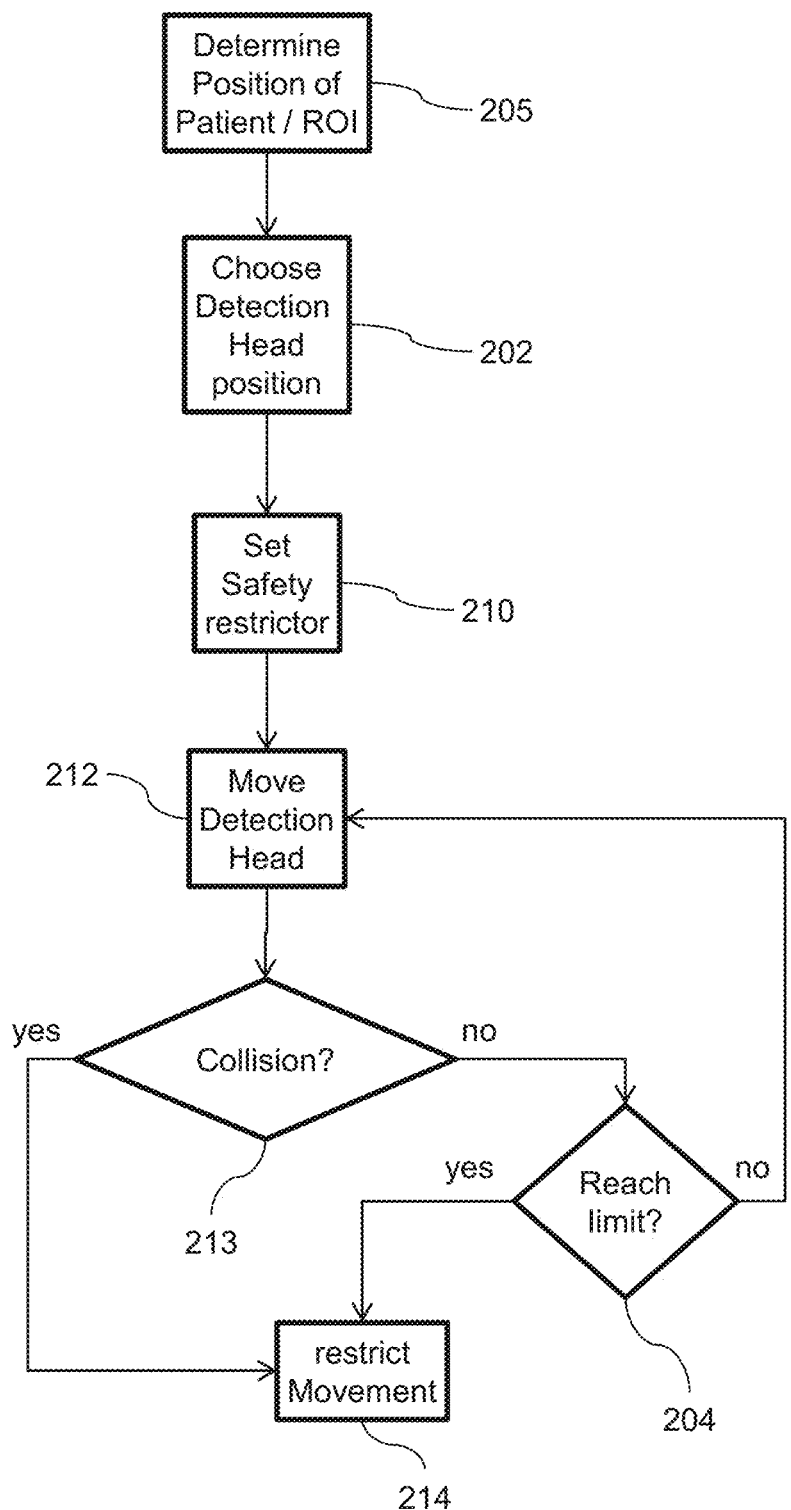
FIG. 2 is a flow chart of a method of avoiding a collision in accordance with an embodiment of the current invention.
Figure 12:
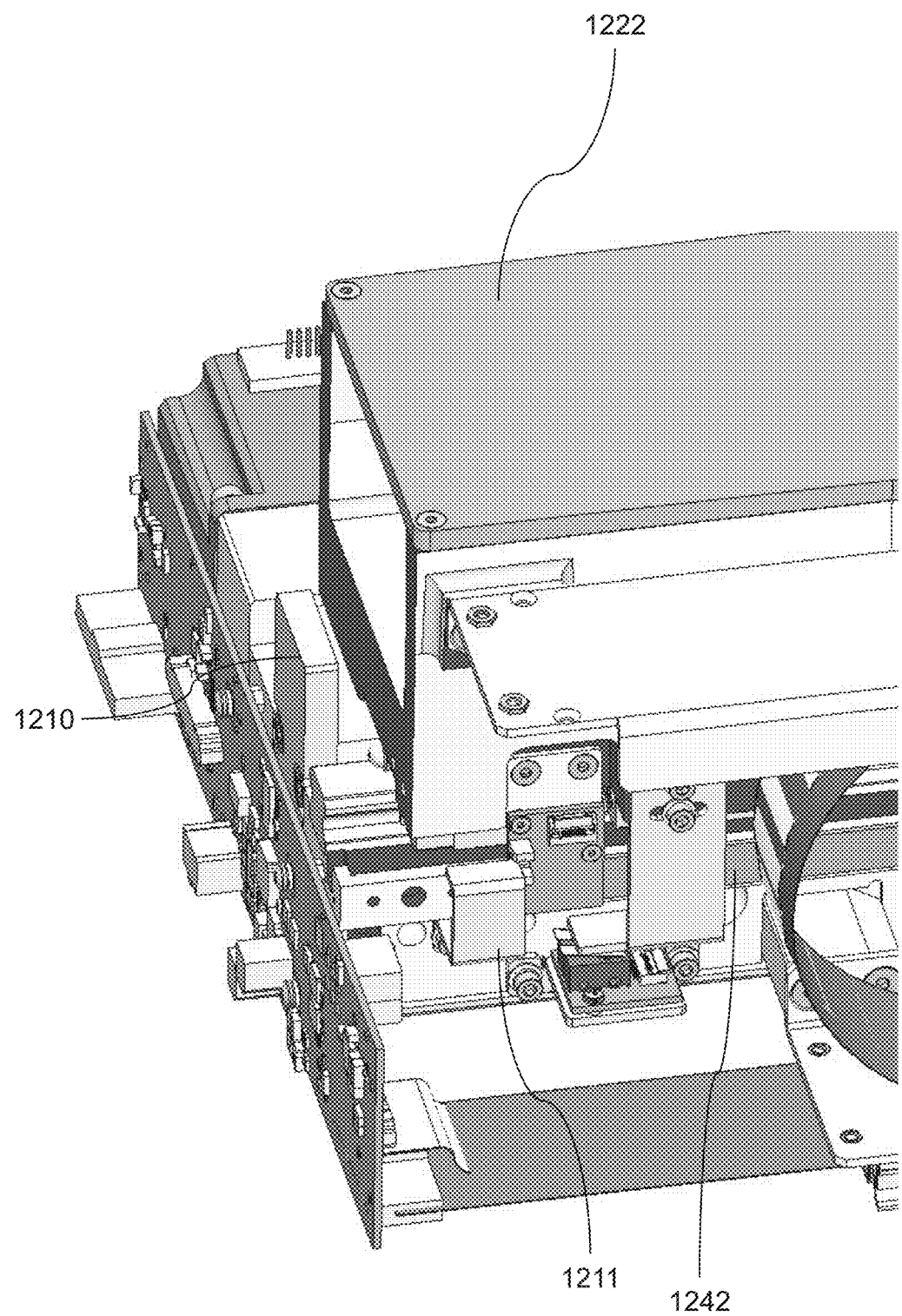
FIG. 12 is a perspective view of a few optional safety restrictors in accordance with an embodiment of the current invention.
Figure 13:
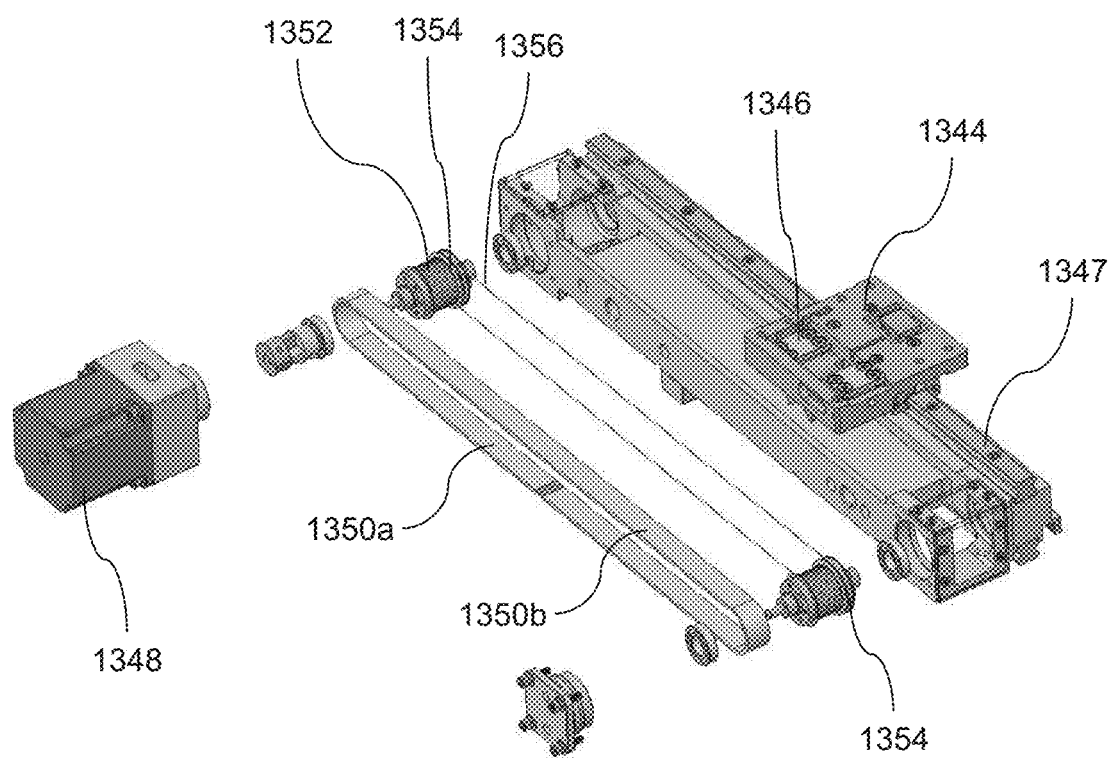
FIG. 13 is a perspective view of a safety movement restrictor in accordance with an embodiment of the current invention.

In some embodiments, a sensor circuitry 106 may sense a location of an object (for example a patient, a ROI and/or a region to protect) independently of a shield. For example, sensor circuitry may include an ultrasound ranging sensor, a laser ranging sensor and/or a magnetic sensor FIG. 2 is a flowchart illustration of a method of preventing collision in accordance with an embodiment of the current invention. In some embodiments a safety mechanism may include a positioning control mechanism(for example an actuator 1348 for example as illustrated in FIG. 13 and/or a position indicator (for example an encoder 1242 as illustrated for example in FIG. 12 and/or a switch 1211 for example as illustrated in FIG. 12) and/or a sensor (for example as described with respect to sensor 104).

In some embodiments, the position of a significant object (for example patient and/or a region to be protected and/or a region of interest) is determined 205. For example, the position of the patient and/or the ROI may be supplied by a practitioner and/or by a marker and/or by a imager (for example an IR imager and/or a visible light imager and/or a microwave imager). Based on the position of the significant object, a head position chosen 202 (e.g. the head position may include a desired location for the head and/or a limit to movement of the head).

In some embodiments, after choosing 202 the limits to the head position, a restrictor is set 210. Optionally, the restrictor is set before moving 212 the detector head and/or while moving 108 the detector head. For example, setting 210 a restrictor may include selecting a restricting location and/or activating a physical motion stopper (for example a physical stopper may be connected to an actuator which positions the stopper in a path of movement of a head movement mechanism).

Alternatively or additionally, setting 210 a restrictor may include initiating a movement restriction routine. For example a movement restriction routine may include selecting an indicator that a limit to movement has been reached 204 and/or setting a watchdog. For example, the watchdog may restrict 214 movement in response to an indicator that a limit has been reached 204 (for example by stopping and/or slowing movement). For example, an indicator that a limit has been reached 204 may include a prescribed movement of an actuator. For example, an indicator that a limit has been reached 204 may include an output of an encoder indicating that the position has been reached 204. For example, an indicator that a limit has been reached 204 may include activation of a switch indicating that the position has been reached. For example, an indicator that a limit has been reached 204 may include a signal from a proximity detector indicating that the detection head a approached to within a chosen distance of a ROI and/or a protected portion of a patient.

In some embodiments, movement may be restricted 214 upon an error indication (for example indication of a collision 213). For example restricting movement may include stopping movement and/or restricting a rate of movement and/or reversing a movement. Optionally, setting 210 a restriction condition may include setting a watchdog on a collision detector.

Figure 3:
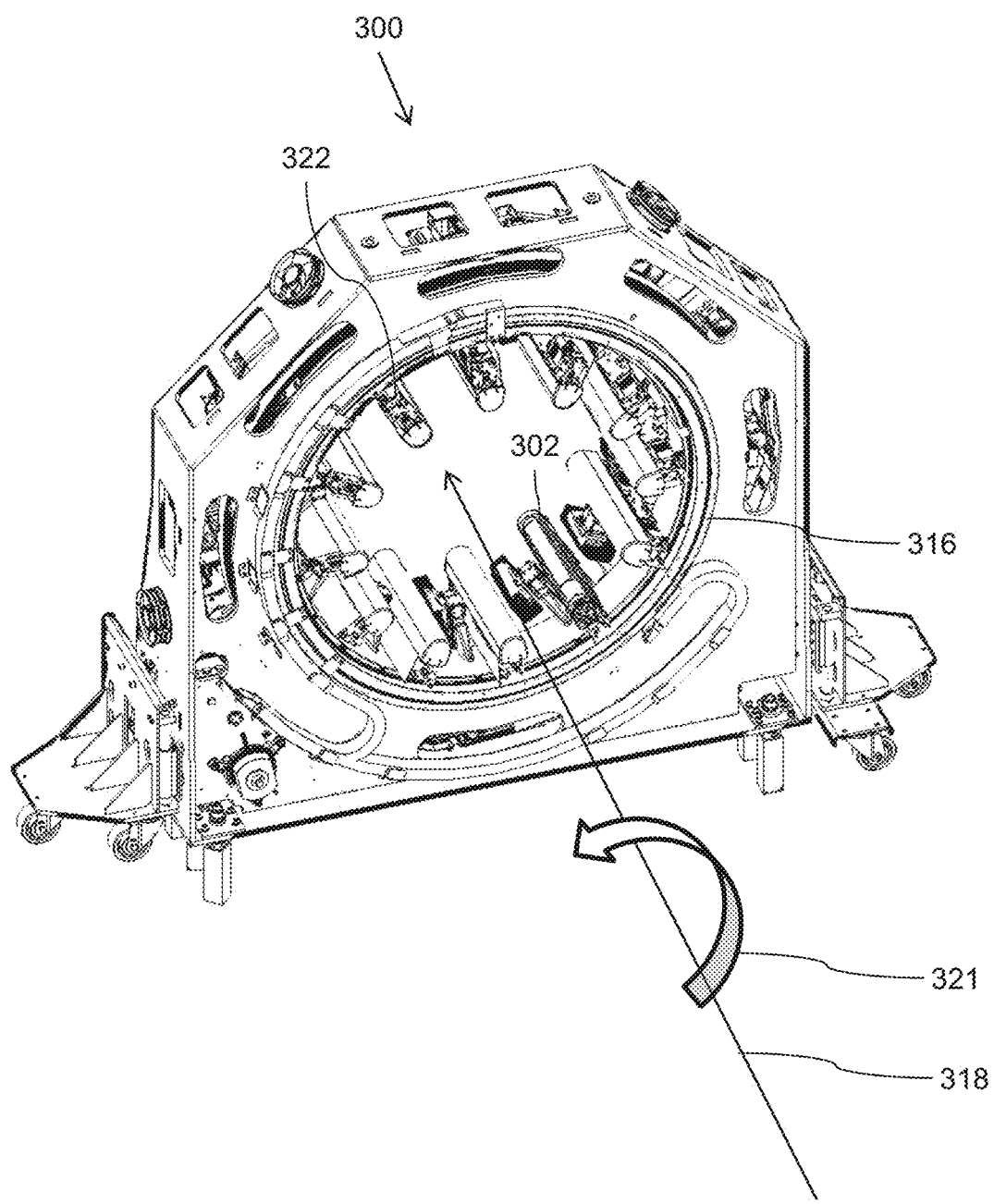
FIG. 3 is a perspective drawing of a close range tomographic scanning machine in accordance with an embodiment of the current invention.

FIG. 3 is a perspective drawing of a close range tomographic scanning machine 300 in accordance with an embodiment of the current invention. For example, a close range tomographic scanning machine may include a volumetric scanner (for example as described in U.S. Pat. No. 8,338,788), a CAT scanner, a PET scanner, a CT scanner, a MRI scanner, an Ultrasound scanner, a Laser 3D scanner, a SPECT scanner, a nuclear medicine tomography system (for example as described is U.S. Patent Application Publication No. 2015119704) a gamma camera and/or other tomographic devices (for example as described in U.S. Patent Application Publication 20100061509).

Figure 4A:
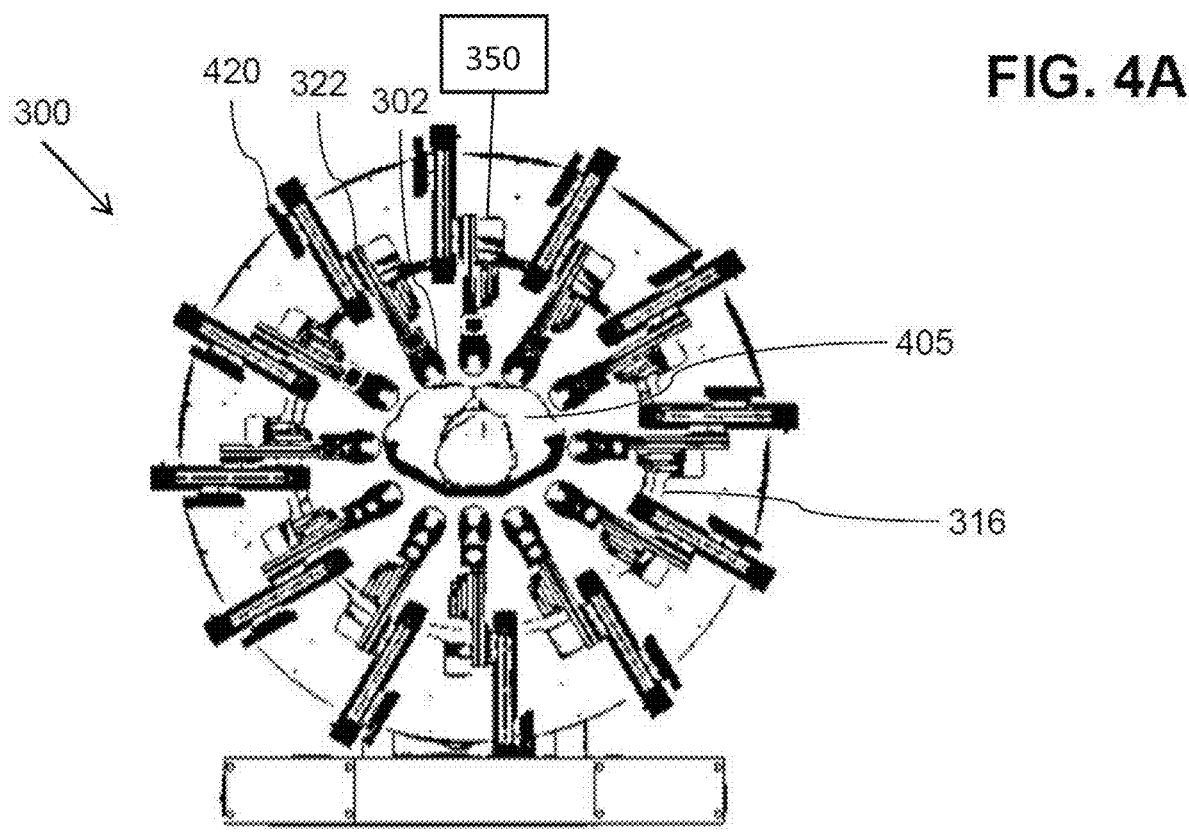
FIGS. 4A and 4B are perspective drawings of a close range tomographic scanning machine scanning a torso and a head respectively of a subject in accordance with an embodiment of the current invention.
Figure 4B:
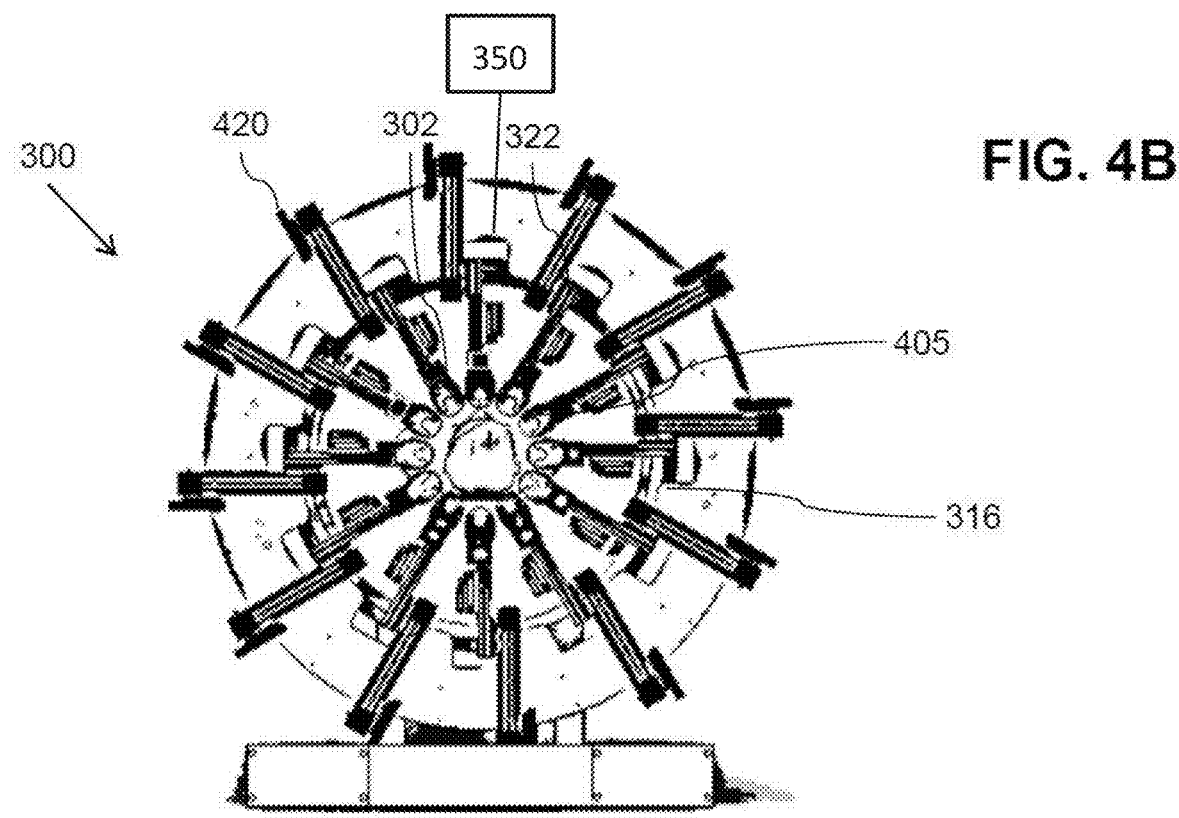

FIGS. 4A and 4B are perspective drawings of a close range tomographic scanning machine scanning a torso and a head respectively of a subject in accordance with an embodiment of the current invention.

In some embodiments machine 300 includes a mechanism for extending and retracting a detector head 302. For example, detector head 302 located at one end of an arm 322, which is movably mounted on to extend radially on a gantry 316. Within or (optionally) attached to the arm 322 is an actuator (for example motor 1348 of FIG. 13 and/or a linear actuator). Control of extension and retraction is optionally provided by system controller.

In some embodiments, each detector head includes a sensor array (e.g. a pixel array). In some embodiments, the array includes a semiconductor pixel array where, in some embodiments, the semiconductor is cadmium zinc telluride (CZT).

In some embodiments, the sensor array is arranged on a surface, where the surface is pivotable, around one or more axis of the surface, with respect to an axis of extension and/or retraction of the detector head (e.g. an axis of the arm associated with the detector head). In an exemplary embodiment, the pivot axis is orientated parallel to an axis of the device e.g. of a patient support e.g. an axis of rotation of the gantry.

In some embodiments a balancing mechanism is supplied, for example to balance the weight of detector head 302. For example a weight 420 is provided to balance the weight of detector head 302. Optionally, radial movement of head 302 is coupled to movement of weight 420. For example, head 302 and weight 420 may be coupled to move in opposite directions along parallel tracks. Optionally, coupling may be by a suitable pulley arrangement and/or belt or cable or in any other suitable and/or desired manner (for example as illustrated in FIG. 13). For example, the weight of detector head 302 may be between 0.5 Kg and 30 Kg, for example, between 3 Kg and 20 Kg, for example, 7 Kg. Optionally, the moving part of the head weighs between 1 and 30 Kg. Optionally, the entre arm module weights between 2 and 50 Kg, for example, between 5 and 30 Kg.

In some embodiments, balancing the weight of detector head 302 allows use of a very small force for extension and retraction while gravitation does not produce any motion or resistance since the counterweight provides a balancing counter force equal to the projection of the total force (vector) along the path of linear motion.

In some exemplary embodiments, for a detector head weighting about 20 kg, counter-balance can be provided by a weight of approximately 19.5 kg, so a force of only about 0.5 kg will be needed to be employed for moving the detector head.

In some embodiments, Gantry 316 rotates, for example, to allow circumferential position of detector head 302. Gantry 316 is optionally rotationally counter balanced. For example, counter balanced rotation to enable use of small compact motion systems, and easy manual movements in case of emergency.

In some embodiments, counter balanced motions allow use of gentle forces to cause the motion. Optionally gentle force potentially reduces risk of patient 405 injury in case of a collision. Alternatively or additionally, in case of a collision, the patient 405 can typically easily resist such gentle force and/or move the detection head away regardless of their orientation. In some embodiments, balancing forces enables moving heavy parts and/or clearing a patient 405 from the machine in case of emergency.

In some embodiments, strict positional requirements and/or limitations are dynamically placed on a detection head of a close range tomographic scanning device. For example, it may be desired by place a detection head 302 very close (for example within 5 cm and/or within 1 cm and/or within 10 cm and/or within 30 cm of a ROI). On the other hand there may strict limitation on and/or a force of impact of the head with the patient 405 (e.g. the ROI). In some embodiments, as the detector head scans a ROI (for example moving longitudinally 318, radially and/or rotating 321 around an axis of a patient 405), precise coordinated movements may facilitate retaining the desired scan distance and/or avoiding impact. In some embodiments, a patient 405 may move and/or may feel a need to escape the device, further complicating control of movement of the machine 300.

In order to protect a patient 405 from harm from impact and/or contact with dangerous electrical currents, a safety system may be provided. For example, the safety system may include dynamically programmable limitations of movement and/or multiple layers of indicators of hazardous conditions and/or limitations on movement.

The multi-faceted system may protect the patient 405 and/or facilitate precise positioning of a detector head at close proximity to a patient 405. For example, a proximity sensor may be used to guide positioning of the head and/or continue movement until the head is close enough to a ROI. Alternatively or additionally the proximity sensor may sense when the head is endangering the patient 405, for example by approaching too close and/or too fast.

Back up dynamic movement restrictors may be supplied to prevent hazardous conditions. For example, when the proximity sensor is too slow and/or inaccurate, a movement restrictor may prevent hazardous conditions. The movement restrictors may be dynamically set during a scan to allow changes in position according to body contours during the scan and/or due to patient 405 movement and/or as more precise position information is acquired and/or in response to recalibration. A collision sensor optionally adds another layer of protection and/or redundancy to protection. The safety systems are optionally configured to reduce interference with measurements of the detection head.

In some embodiments, control interfaces are configured for ease of use and/or safety. For example a touch screen interface may be supplied to a patient 405 to allow him to contact technical personnel and/or retract a detection head and/or escape the machine. For example, a touch screen interface may be supplied to technical personnel. Optionally the touch screen interface will integrate information to reassure a user when the device is working properly, warn the user when the device is not working properly and/or allow simple control of the device when desired. Alternatively or additionally, the control interface may test user reactions and/or generate a warning when a user is not reacting properly. For example, if there is no response to an inquiry and/or there is no action over a prescribed time limit, the user interface may generate a warning condition and/or an ameliorative regime.

FIG. 5 is a perspective drawing of a detection head 502, an extension arm 522, a proximity sensor 530 and a collision sensor including a shield 504 and a support structure 532 in accordance with an embodiment of the current invention. A counter weight 520 optionally moves opposite the detector head 502.

In some embodiments a detector head has a FOV 508 passing through a surface of the shield 504 and/or proximity sensor 530. For example the detection may scan by rotating over an arc 507 inside of shield 504. Optionally shield are shaped to preserve a substantially constant distance from head 502 along its scanning range (e.g. FOV 508). For example, within FOV 508, the surface of shield 504 and/or sensor 502 may be positioned less than 1 cm and/or between 1 to 3 cm and/or 3 to 5 cm and/or between 5 to 10 cm from head 502.

Figure 8:
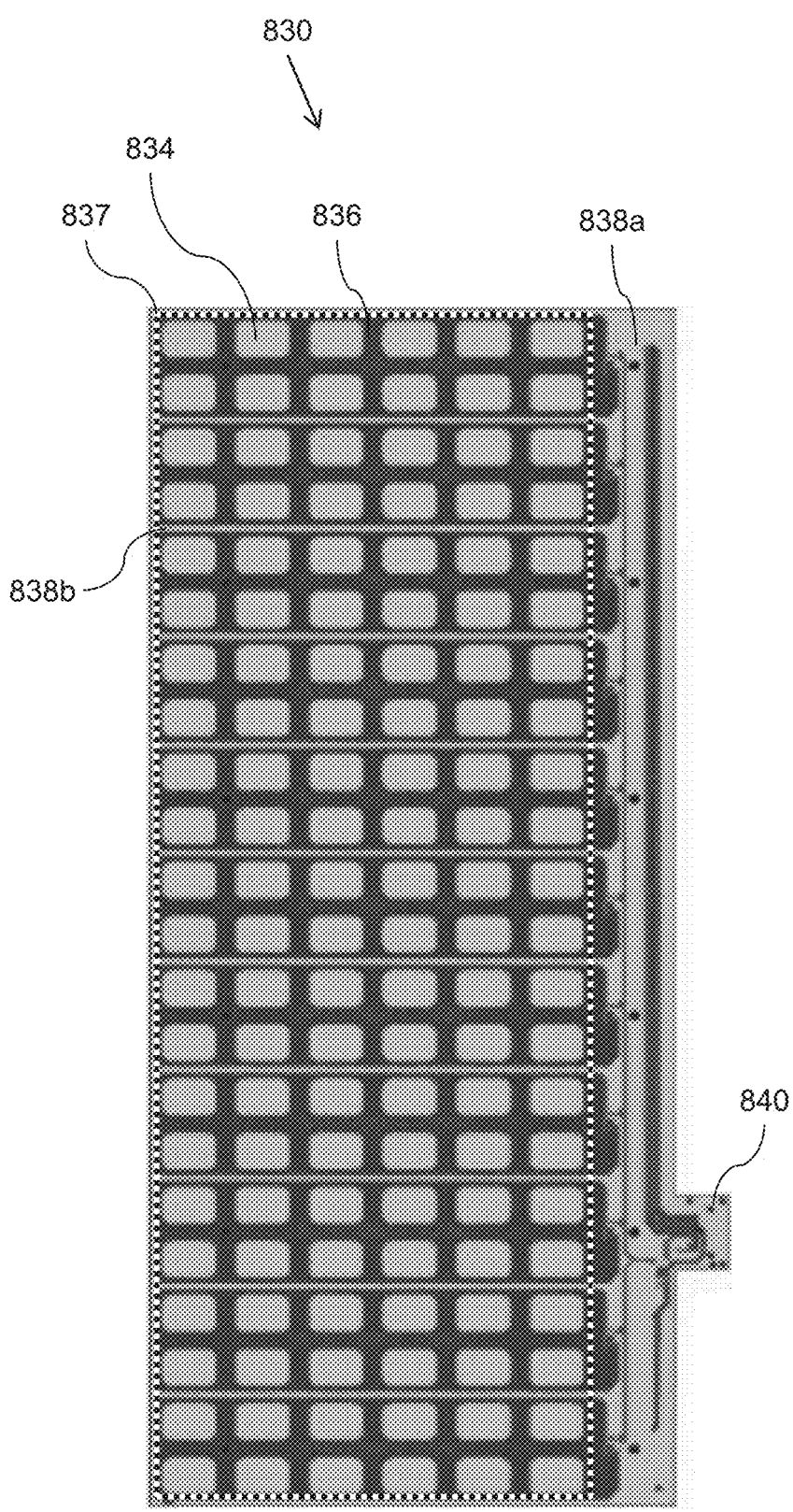
FIG. 8 is a top view of a proximity sensor in accordance with an embodiment of the current invention.

In some embodiments, shield 504 and/or sensor 530 are configured to reduce interference with detection of a signal. Optionally, components of the proximity sensor and/or collision sensor that may interfere with a signal may be positioned away from a FOV of the detector (for example as illustrated in FIGS. 8 and/or 11). Alternatively or additionally, shield 504 and/or sensor 530 may be configured to interfere with a signal in a way which give a signal that can easily be reconstructed. For example, interference may be homogenous and/or constant across the FOV 508. For example, materials that interfere with a signal may distributed substantially homogeneously across FOV 508 (for example as illustrated in FIGS. 6-10, 16.

FIG. 6 is a is a perspective drawing of a collision sensor shield 504 in accordance with an embodiment of the current invention. Optionally, the portion of the shield in the FOV of the detector head is made of a material that is nearly transparent to the signal being detected. For example the shield may be made of fiber glass and/or fiber. Alternatively or additionally, the portion of the shield in the FOV of the detector head is made of material having homogeneous properties with regard to interference with the signal being detected. For example, this may facilitate reconstruction of the source signal and/or source location based on the signal detected. For example, structures that would cause a large and/or non-homogenous change in the detected signal (for example a mounting plate 536 and/or associated stiffening elements) may be positioned outside of the FOV of the detector head.

FIG. 7 is a perspective drawing of a proximity sensor 530 and a shield 504 in accordance with an embodiment of the current invention. Optionally the proximity sensor 530 may be flexible. For example, proximity sensor 530 is flexed to fit the contour of shield 104 and/or to conform to the scanning arc 507 of the detector head. For example, sensor 530 is flexed such that the surface sensor 530 is approximately the same distance (e.g. the distance between the scanning head and the proximity sensor may vary less than 5% and/or less that 20% and/or less than 50% and/or less than 100% over the more than 95% of the FOV and/or over more than 70% of the FOV). For example, the proximity sensor 530 may be used to detect a hazardous condition (for example the detector head approaching a patient too fast and/or too closely). For example, the proximity sensor 530 may be used to determine the distance between the scanning head and the ROI. In some embodiments, determining the distance between the detection head and the ROI may be facilitated by the fixed distance between the detection head and sensor 530.

In some embodiments a portion of the proximity sensor covers a significant portion of the FOV of the detector heads. For example, the significant portion of the FOV of the detector head may include at least 95% and/or at least 80% and/or at least 50% of the FOV of the detection head. Optionally, the portion of the proximity sensor 530 covering the significant portion of the FOV of the detection head may have a nearly constant interference with a detected signal. For example, the attenuation of the detected signal over the covering portion of the proximity sensor may vary by less than 5% and/or less than 10% and/or less than 20% and/or less than 50% along at least 95% and/or at least 80% and/or at least 50% of the surface of the covering portion of the proximity sensor.

In some embodiments, a portion of the proximity sensor 530 is positioned between the detector head and a patient. For example, a portion of the proximity sensor 530 may be positioned between the detector head and the ROI. For example, a portion of the proximity sensor may cover at least a portion of the FOV of the detector head.

FIG. 8 is a top view of a proximity sensor 830 in accordance with an embodiment of the current invention. For example, proximity sensor 830 is a capacitance sensor. Optionally, sensor 830 includes a layer of conductive islands 834 on an insulting layer 836 (for example, visible portions of the insulating layers are represented as dark regions in FIG. 8). Optionally, islands 834 are connected via connection lines 838*a*, 838*b* to a sensing circuitry 840.

Optionally, the proximity sensor 830 may include a covering portion 837 (for example delimitated by the broken white line in FIG. 8). For example the covering portion 837 may cover a significant portion of the FOV of a detector head. Optionally a portion of the sensor 830 may be outside the FOV of the detector head. For example, some islands 834 and/or some connecting lines 838*b* may be in the covering portion 837. Optionally some connecting lines 838*a* and/or a sensing circuitry 840 may be located outside the covering portion 837.

Figure 9A:
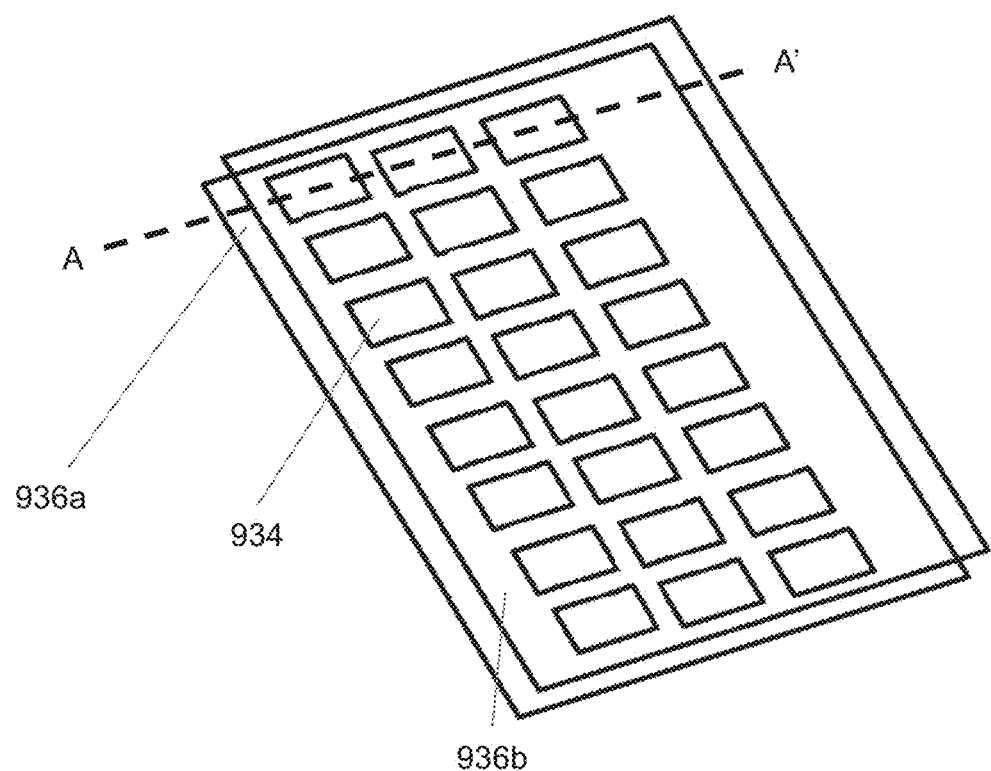
FIGS. 9A and 9B are a schematic perspective view and a cross sectional view respectively of a proximity sensor in accordance with an embodiment of the current invention.
Figure 9B:
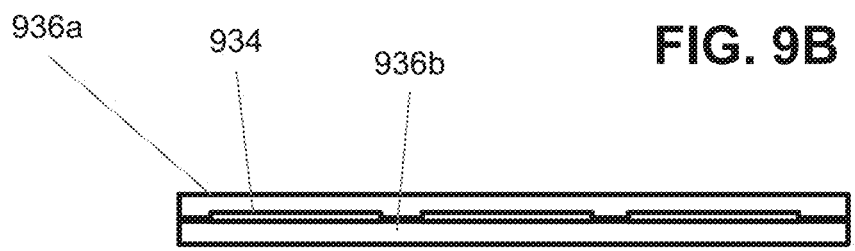

FIGS. 9A and 9B are schematic perspective and cross sectional (cut along line A-A') views respectively of a portion proximity sensor 930 in accordance with an embodiment of the current invention. For example, a conductive layer including islands 934 and/or connecting lines may be supported on and/or sandwiched between one or more insulating layers 936*a*, 936*b*. Some embodiments may include a further layer. For example, a further layer may include conductive connecting lines that may be in selective electrical contact with some of the islands 834 and/or a sensor circuit.

In some embodiments, the conductive islands 834 and/or connecting lines and/or sensing circuit may form a capacitive proximity sensor array (for example a projective capacitive array). Each conductive island 834 may pick a capacitive charge when brought close to a capacitive object (for example a ROI and/or a patient). The change in charge may be sensed by the sensing circuit and interpreted to determine the distance to and/or location of the capacitive object.

Figure 10:
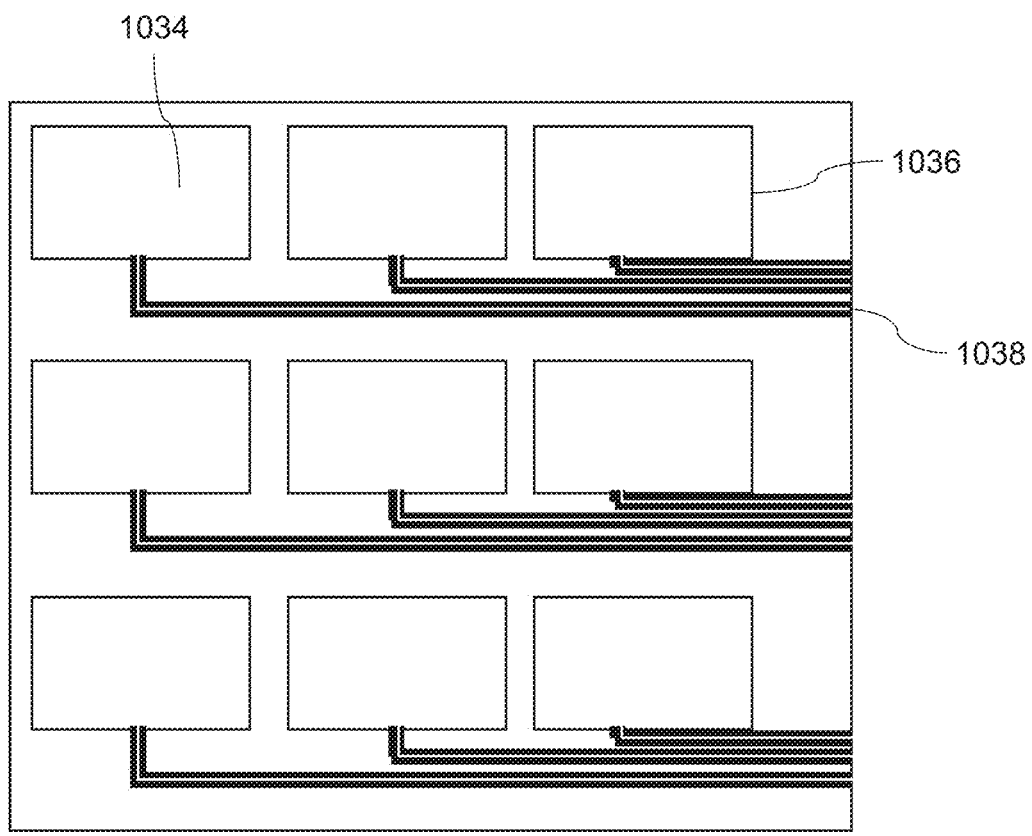
FIG. 10 is a schematic overhead view of a conductive layer of a proximity sensor in accordance with an embodiment of the current invention.

FIG. 10 is a schematic overhead view of a conductive layer 1039 of a portion of a proximity sensor covering a FOV of a detector head in accordance with an embodiment of the current invention. Optionally the conductive layer 1039 is mostly homogeneous. For example, the conductive layer in the covering portion may include islands 1034 and/or connective lines 1038 separated by thin cut out lines 1036. For example the width of more than 95% of cut out lines 1036 in a layer 1039 may be may be less than 0.01 mm and/or less than 0.1 mm and/or less than 1 mm and/or less than 1 cm. For example, conductive islands 1034 and/or conductive transmission lines 1038 may cover more than 99% and/or more than 97% and/or more than 95% and/or more than 90% and/or more than 80% and/or more than 70% and/or more than 50% of the surface area of layer 1039.

Optionally the conductive layer 1039 acts like a homogeneous conductive sheet with respect to a detected signal. Optionally, connecting lines 1038 in layer 1039 supply connection between islands 1034 and a sensor circuit (for example circuit 840) outside the FOV of a detector head. For example the proximity sensor may not have further wires and/or may have few further wires interfering with the FOV of the detection head. Alternatively or additionally, a separate layer of connector lines may include a nearly homogenous sheet of conductor with thin cut outs. For example the layer of connector lines may be made of homogenous conductor material covering more than 99% and/or more than 97% and/or more than 95% and/or more than 90% and/or more than 80% and/or more than 70% and/or more than 50% of the surface area of the layer.

In some embodiments, conductive layer is part of a multilayer structure including one or more insulting layers and/or a further layer of connecting lines for example as illustrated in FIGS. 9A-9B. Optionally, layer 1039 and/or the entire multilayered structure may be flexible and/or formed to match a shield of a detection head and/or a FOV of a detection head for example as illustrated in FIGS. 5-8. Optionally the insulating layers may transparent and/or homogenous with respect to the detected signal. For example the entire multilayered structure may have a nearly homogenous effect on a signal coming to the FOV of the detector head.

In some embodiments, output from a proximity sensor is used by an automated guidance system. For example, the guidance system may include a processor configured to bring the detection head to a desired proximity to a ROI. Output of the proximity sensor may be used to guide the detection head to a desired proximity to a ROI and to determine when the detection head has reached a desired proximity to a ROI. Alternatively or additionally, a proximity sensor is used to inhibit impact with a patient and/or other collisions. For example, output of the proximity sensor may be received by a watchdog that restricts movement of the detection head when the proximity output indicates that the head is approaching to fast and/or too close to a patient and/or a ROI and/or another object.

Figure 11:
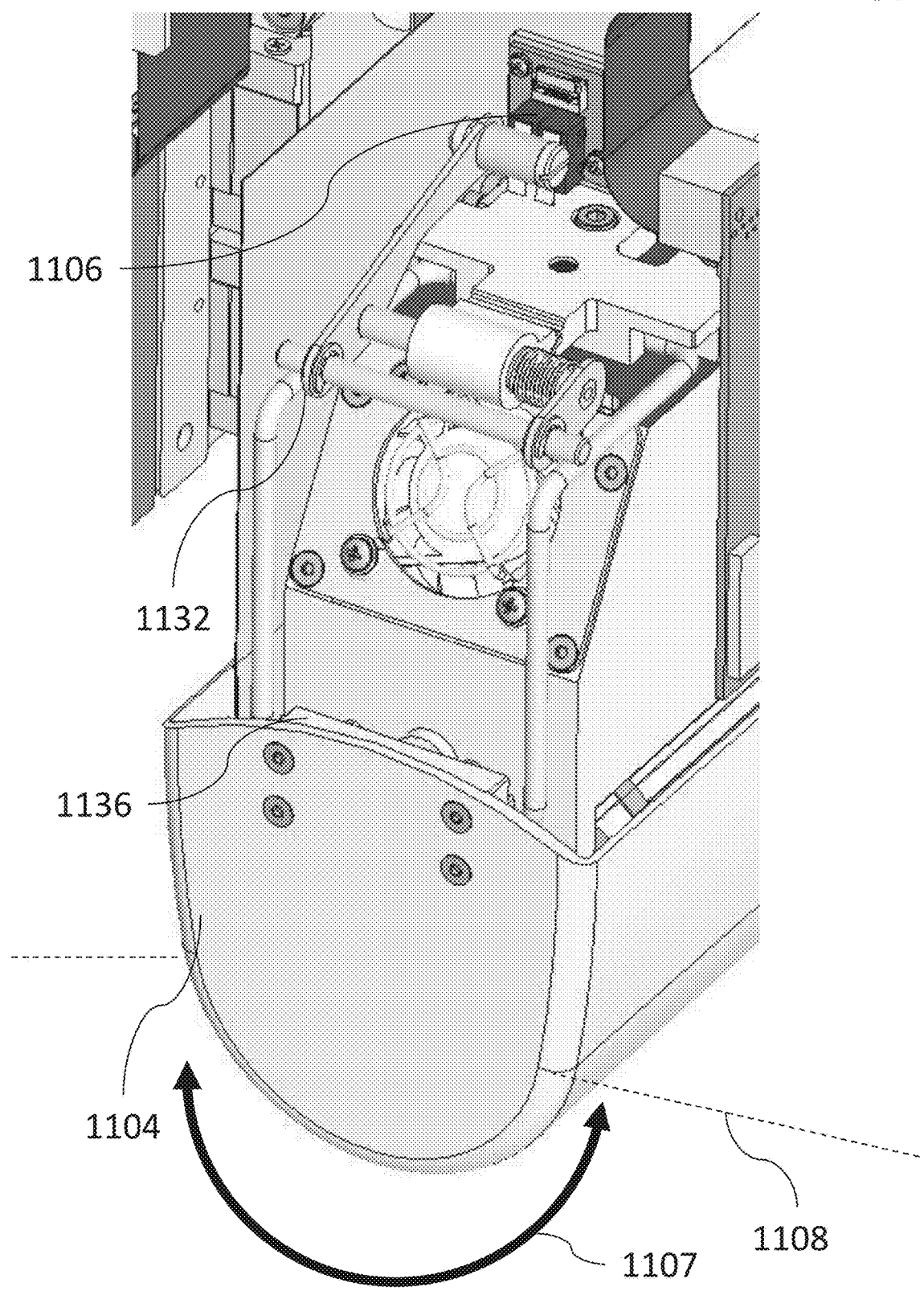
FIG. 11 is a perspective view of a collision sensor head connected to a support and/or a sensor circuit in accordance with an embodiment of the current invention.

FIG. 11 is a perspective view of a collision sensor connected to a support and/or sensor in accordance with an embodiment of the current invention. In some embodiments a collision sensor includes a shield 1104 that covers a FOV 1108 and/or a scanning arc 1107 of a scanning head. Optionally shield 1104 is configured to reduce interference with a measured signal and/or to facilitate reconstruction of the source signal from the detected signal for example as described with respect to shield 504 of FIGS. 5, 6, and 7. Additionally or alternatively, the collisions sensor includes a mounting plate 1136 and/or a support 1132 for shield 1104. Additionally or alternatively, the collisions sensor includes a sensor circuit 1106 (for example including a stress or strain sensor e.g. a position sensor e.g. position sensing device PSD). For example, sensor circuit may sense a stress and/or strain on support 1132 caused by an impact between shield 1104 and another object (for example a patient and/or a ROI). Optionally, mounting plate 1136 support 1132 and/or senor circuit 1106 are positioned outside of FOV 1108. For example, positioning support 1132 and/or senor circuit 1106 outside of FOV 1108 may reduce the interference that support 1132 and/or senor circuit 1106 cause to a detected signal.

In some embodiments, sensing circuit 1106 sends output to a watchdog. For example the watchdog may be programed to restrict movement of the detection head when a stress or strain is detected. For example, when a stress or strain indicating a sufficient impact (for example between 1 kg force to 3 kg force between 3 kg force to 5 kg force between 5 kg force to 10 kg force and/or greater than 10 kg force), the watchdog may stop movement of the detection head and/or reverse movement of the detection head and/or return the detection head away from the patient. The action of the watchdog may depend on the force of the impact and/or on other factors (for example the watchdog may include a multifactor watchdog). The structure of support 1132 and/or sensing circuit 1106 may be configured to be equally sensitive to forces in all directions and/or applied on any position on shield 1104. Alternatively or additionally, support 1132 and/or sensing circuit 1106 may be configured to more sensitive to forces in one direction and/or applied at one position than in another direction and/or applied at a different point on the shield.

FIG. 12 is a perspective view of some position control mechanisms in accordance with embodiments of the current invention. Optionally, a detector positioning system may include one or more physical position control mechanisms including for example a mechanical stop 1210 and/or an encoder 1242 and/or a sensor flag 1211 (for example, including a microswitch that is activated when a detection head reaches a predetermined position).

In some embodiments, a safety stop may be set dynamically. For example, after determining a scan position for the detection head, a controller may determine safety limits (for example based on the location of the patient and/or the safety heads). Where, in some embodiments, the location of the patient and/or detector heads is provided to the controller by one or more proximity sensor. Where, in some embodiments, alternatively or additionally, where detection head location is expected location e.g. from motor control signals and/or measured location e.g. measured by one or more encoder configured to measure detector head movement/s.

For example, in some embodiments, a mechanical stop may be set (e.g. stop 1210) to prevent possible impact with the patient (e.g. in some embodiments, a position of stop 1210 is adjustable). Optionally, in some embodiments, one or more safety stop (e.g. including one or more mechanical stop) is set in an initial period of high speed movement and/or a period of realignment of the detection head.

In some embodiments, a mechanical stop may include a block (for example stop 1210) and/or a cable. Optionally position of the block may be set dynamically to allow safe movement to a position that is determined at the time of scanning depending on body contours and/or movement of a patient. Alternatively or additionally, there may be multiple position blocks in the system, according to the determined limit to movement and/or desired scanning position, some of the blocks may be activated (for example an actuator may move a block between an activated (blocking) position and/or a deactivated position (where the positioning of the detector head is not affected by the block)). Alternatively or additionally a mechanical stop may include a cable. For example the effective length of the cable may be adjusted dynamically. For example, slack may be added to the cable (e.g. before movement) e.g. to allow the detector head to move further e.g. to move in closer to a patient. Optionally, a mechanical stopper may be installed in a location of reduced force, for example, where a counter balance assists in the desired restriction on movement of an extension arm 1222. Optionally, a mechanical stopper may limit movement in one direction. For example, a cable and/or stopper may be configured to prevent extension of a scan head toward a patient past a specified location but may allow movement away from the patient without limitation.

In some embodiments, as the head approaches a scan position, a more precise guidance system will be employed to move the detector head to a final close-in scanning position. For example, guidance to a final scan position may be based on a proximity sensor. Optionally, a watchdog may be activated to limit speed of movement and/or to monitor a proximity sensor to avoid collision. Optionally, the mechanical stop may be deactivated as the scan head approaches the scan position (for example, to allow more precise positioning based on the proximity sensor).

In some embodiments an encoder may be used to limit positioning and/or movement (for example speed) of a detection head. For example, a watchdog may be coupled to the encoder to restrict movement. Alternatively or additionally one or more torque limiter may be used to restrict dangerous forces in the system.

In some embodiments close range tomographic scanning machine may include a system to aid in clearing a patient from the machine. Optionally, a detection head may be biased away from the patient. For example, if there is a system failure (for example due to a power failure, the detection head may retract away from the patient facilitating clearing the patient from the machine. For example, a biasing element may include an elastic force element (for example a spring) may be used to bias the detection head away from the patient.

FIG. 13 is a perspective view of a movement restrictor in accordance with an embodiment of the current invention. In some embodiments a weight of a detector head is counterbalanced by a balance mechanism (for example to facilitate soft movement and/or manual pushing away of the detector head, for example, as explained with respect to FIGS. 4A and 4B).

Optionally, a movement restrictor (including for example a sensor cord 1356 and a brake mechanism 1352) restricts movement of the detector head when movement is uncoordinated to the counterbalance.

In some embodiments, movement of a detector head is tied to a counter balance. For example, a belt 1350a, 1350b coordinates movement between a detector head and a weight. For example, movement of a counter weight and a detection head may move on two respective trollies 1344 connected to parallel tracks 1347 (only one trolley 1244 is visible in FIG. 13). The trollies may be connected each to an opposing side 1350a and 1350b of a belt e.g. by clips 1346 (e.g. a first trolley is connected to a belt first opposing side 1350b and a second trolley (not illustrated) is connected to a belt second opposing side 1350a). When one trolley 1344 moves in one direction, the belt 1350a, 1350b pulls the other trolley in the opposite direction.

In some embodiments, no matter with direction the tracks 1347 are directed, (e.g. a weight of the counterbalance and/or difference in weight between the counterbalance and the detection head is selected so that) the force of gravity on the detection head is counterbalanced by the force from the weight. Optionally, an actuator (for example stepper motor 1348) drives movement of the detection head. For example, stepper motor may drive movement of belt 1350a, 1350b. Optionally, the balanced forces on the detection head facilitate driving movements of a heavy detection head with gentle force. For example, a detection head may be moved radially (and/or vertically upward) employing a force that is one tenth or less the weight of the detection head, or 1/50-1/5 m, or 1/20-1/10 or lower or higher or intermediate ranges or fractions of the weight of the detection head. For example, a discrepancy between the weight of the detection head and a counterbalance is 1-50%, or 1-20%, or 1-10%, or 0.5-10%, or 0.5-5%, or lower or higher or intermediate ranges or percentages. For example, a detection head of mass between 15 to 50 kg and/or weight of 150 to 500 N may be driven radially (including vertical depending on the angle of the gantry) using a force of between 15 to 50 N and/or less than 15 N.

In some embodiments, one or more sensor is sensitive to a condition of the linkage (linkage which, e.g. connects the detection head to the balancing mechanism) and/or to movement of the weight and/or the detector head. For example, a safety cord 1356 is sensitive to the condition of belt 1350a, 1350b. in some embodiments, a loss of tension of the belt 1350a, 1350b (e.g. a reduction of tension below a threshold e.g. as measured by a sensor sensing belt tension and/or identified by a controller receiving the sensor signal) and/or a movement of the detector head that is not coordinated to a movement of the weight results in sensor signals which a controller recognizes (e.g. compares with a threshold) and generates a control signal instructing restriction of movement of the sensor head. For example, a sensor cord 1356 may be connected between guides 1354 of the belt 1350a, 1350b. Optionally, guides 1354 may include rollers, and/or a track and/or a guide wheel. When then belt 1350a, 1350b is functioning properly, guides 1354 move in tandem.

Should anything happen to the balance between the weight and the detector head (for example if belt 1350a, 1350b where to snap and/or if clips 1356 fail and/or if the belt stretches beyond a threshold) the tension on at least one end of belt 1350a, 1350b will be reduced and/or released, releasing at least one of guides 1354.

Optionally guides 1354 are biased to twist in opposite directions when freed from belt 1350a, 1350b putting tension on (e.g. increasing tension on) sensor cord 1356. For example, cord 1356 may be connected to a brake, such that tension on cord 1356 (e.g. over a threshold) activates the brake (e.g. a flywheel break coupled to the belt and/or cord) and/or locks trolley 1344 to track 1347 preventing uncoordinated movement of the weight and/or the detector head.

Alternatively or additionally, a change in tension on sensor cord 1356 may trigger an alert (e.g. through one or more a system user interface) to a user when uncoordinated movement and/or braking occur. Alternatively or additionally, a retraction mechanism may allow and/or cause retraction of a detection head away from a patient upon stimulation of the sensor (e.g. cord 1356) and/or activation of the movement restricting mechanism (e.g. the safety brake).

In some embodiments, one of guides 1354 may be linked to movement of the counter balance directly (for example not only via belt 1350a, 1350b) and/or another guidewheel 1354 may be linked to movement of the detector head directly (for example not only via belt 1350a, 1350b). For example, non-coordinated movement of the detector head and the counter balance may cause cord 1356 to be tightened. Cord 1356 is optionally functionally connected to a braking system that restricts movement of the detector head.

In some embodiments, cord 1356 acts as a redundant belt. If belt 1350a, 1350b fails, cord 1356 prevents uncontrolled movement of the detector head and/or counter balance (e.g. from falling onto a patient) and/or maintains the coordination between movement of the detector head and the counter weight. Alternatively or additionally, cord 1356 is connected to the detection head to a friction brake. When the detection head moves faster than a certain limit the friction brake (e.g. including a flywheel mechanism and/or brake actuator controlled by controller receiving sensor input regarding head position and/or movement e.g. speed) restricts the movement e.g. of cord 1356 and/or belt 1350a-b.

Alternatively or additionally, cord 1356 is connected to the detection head to a wheel 1354. When the detection head moves uncoordinated to wheels 1354, cord 1356 restricts the movement.

In some embodiments, other movement control, safety and/or emergency systems may be coordinated with a force balancing system. For example a biasing element (for example as described above in the description of FIG. 12) may be connected to belt 1350a, 1350b and/or wheels 1354 to bias a detector head away from the patient. For example a linear elastic element (for example a coil spring and/or an elastic band and/or a bungee) may be connected to one part of belt 1350a pulling the belt away from the extended position of the detector head. Alternatively or additionally a torsion spring may be attached to one or both of wheels 1354.

Figure 14:
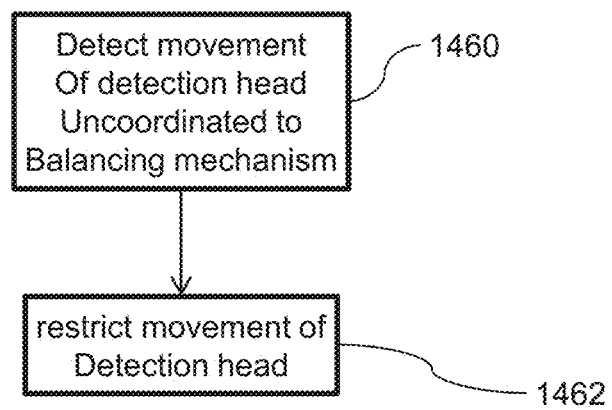
FIG. 14 is a flow chart illustration of a method of restriction of movement of a sensor head in accordance with an embodiment of the current invention.

FIG. 14 is a flow chart illustration of a method of restricting movement of a sensor head uncoordinated to a counter weight in accordance with an embodiment of the current invention. In some embodiments, a movement restricting system is sensitive to coordination between a detector head and a counter balance. Detection 1460 of unbalanced movement triggers restriction 1462 of movement of the detection head. Some exemplary embodiments of such a system are illustrated in FIG. 13 and/or described in the text associated to FIG. 13.

Figure 15:
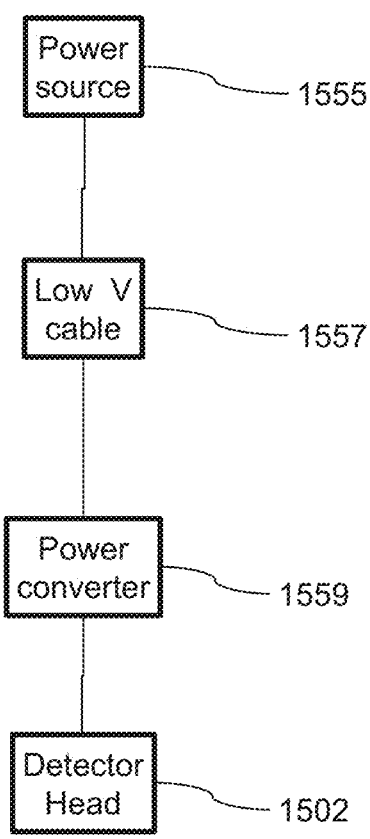
FIG. 15 is a schematic illustration of an improved safety electrical system in accordance with an embodiment of the current invention.

FIG. 15 is a schematic illustration of an improved safety electrical system in accordance with an embodiment of the current invention. In some embodiments, a detector head 1502 may run on high power and/or high voltage. Power for the detector head 1502 is optionally supplied by a power source 1555. Optionally power is transferred from power source 1555 to head 1502 via a cable 1557. Optionally the power in cord 1557 will be limited to a form that does not endanger a patient. For example the power will be supplied at a safe low voltage and high current. Optionally a power converter is located near the detector head that converts the safe power to a power signal that will power the detector. Alternatively or additionally, power supply 1555 may supply power to multiple detector heads. The combined power may be sent as safe signal (e.g. at low voltage). The signal may then be split into lower power signals for each detector head. The lower power signal may then be converted by power converter 1559 to high voltage. Optionally, this will reduce or eliminate dangerous power lines that include enough power and/or voltage to seriously hurt or kill a patient. Additionally or alternatively, power from power supply 1555 may be in the form of an alternating current and/or the patient may be insulated from ground (for example the patient may be supported on a plastic bed).

FIG. 16 is a schematic illustration of an alternative collision detector in accordance with an embodiment of the current invention.

In some embodiments, a collision detector detects contact between an object (an exemplary object indicated by "finger" in FIG. 16) and a detector head. In some embodiments, the object is a portion of a subject and/or subject support surface. Where, in some embodiments, pressure applied to the collision detector closes a space between two powered portions of the detector as indicated in the figure by "ground" and "+" where other power supplies are envisioned and encompassed by the current invention e.g. a charged portion contacting the upper "foam" layer and a grounded portion being at a base of the detector. Where, in some embodiments, the base of the detector is connected e.g. adhered to a detector head.

In some embodiments, an upper portion of the collision detector is electrically insulating and/or or compressible e.g. constructed from foam (e.g. foam rubber) and/or sponge and/or other compressible materials.

In some embodiments, one or more detector head includes a plurality of collision detectors e.g. arranged on the head. In some embodiments, e.g. as described regarding capacitive proximity detector/s, the collision detector covers a FOV region of the detector head and uniformly attenuates a signal (e.g. radiation) detected by the detector head.

General

It is expected that during the life of a patent maturing from this application many relevant technologies will be developed and the scope of the terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A tomographic system comprising:
   a support for a subject in an examination procedure;
   at least one detector head;
   a mobile carrier configured to rotate around said support;
   an extender supporting said detector head on said carrier and dynamically positioning said detector head along a path between said support and said carrier before and/or during performance of a scan;
   a counter weight for said detector head, said counter weight balancing a force of gravity of said detector head along said path;
   a restrictor limiting movement of said extender in response to an unbalanced movement of said head with respect to said counter weight;
   a belt connecting between said detection head and said counterweight;

at least two rollers guiding said belt; and at least one sensor responsive to a malfunction of said belt to trigger said restrictor, where said sensor includes a cord connected between said at least two rollers and measures a change in tension in said cord in response to an uncoordinated rotation of said at least two rollers.

2. The system of claim 1, wherein said malfunction includes a loss of tension in said belt.

3. The tomographic system of claim 1, wherein said unbalanced movement includes one or more of:
movement of said detection head faster than a limit;
change in tension in said belt; and
change in tension in said cord.

4. The system of claim 1, wherein said at least two rollers are biased to rotate in opposite directions, reduction in tension of said belt thereby increasing tension on said cord.

5. The system of claim 1, wherein said restrictor includes a brake configured to inhibit movement of said detector towards said support.

6. The system of claim 1, comprising a brake including an actuator configured to activate the brake, said system comprising:
a controller receiving a signal from said at least one sensor, said controller including circuitry configured to generate a control signal for control of said brake, based on said signal.

7. The system of claim 6, wherein said sensor is configured to measure and said controller is configured to generate a control signal based on one or more of:
tension on one or more of said cord and said belt; and
speed of movement of said detector head.

8. The system of claim 1, wherein said restrictor includes a brake configured to inhibit movement of said detector towards said support;
wherein said brake is activated upon a change in tension on said cord.

9. The system of claim 1,
wherein said restrictor includes a brake configured to inhibit movement of said detector towards said support;
wherein said brake is activated upon a change in tension on said belt.

10. The system of claim 1, comprising a controller receiving signals from said sensor and including circuitry configured to alert a user upon said malfunction in said belt.

11. The tomographic system of claim 1:
wherein said at least one detector head has a field of view including a plurality of directions;
wherein said system comprises:
a shield positioned between said at least one detector head and said support, said shield configured to attenuate a signal detected by said detector uniformly over said field of view; and
a force sensor detecting a force on said shield, said force sensor positioned outside said field of view.

12. The tomographic system of claim 1, comprising:
at least one detector head having a field of view including a plurality of directions; and
a capacitance detector positioned between said at least one detector head and said support, said capacitance detector configured to attenuate a signal detected by said detector uniformly over said field of view.

13. The tomographic system of claim 12, wherein said capacitance detector includes:
a conductive layer configured to uniformly attenuate a signal detected by said detector over said field of view; and a plurality of insulators defining a plurality of isolated islands in said conductive layers, each said island detecting capacitance of a different portion of said field of view.

14. The tomographic system of claim 1, wherein said restrictor includes a brake configured to inhibit movement of said detector towards said support;
wherein said brake is activated upon said detector head reaching a limit position.

15. The tomographic system of claim 1, wherein said at least one detector head and said counter weight are connected by said belt to move in opposite directions in a coordinated manner; and
wherein said unbalanced movement includes uncoordinated movement of the counterweight and detector head.

16. The tomographic system of claim 1, wherein said sensor comprises an encoder.

17. The tomographic system of claim 16, wherein said encoder is used to limit position and/or movement of said detection head.

18. The tomographic system of claim 17, wherein a signal from said encoder provides an input to a watchdog to restrict movement of said detector head.

19. A tomographic system comprising:
a support for a subject in an examination procedure;
at least one detector head;
a mobile carrier configured to rotate around said support;
an extender supporting said detector head on said carrier and dynamically positioning said detector head along a path between said support and said carrier before and/or during performance of a scan;
a counter weight for said detector head, said counter weight balancing a force of gravity of said detector head along said path;
a restrictor limiting movement of said extender in response to an unbalanced movement of said head with respect to said counter weight;
a passive biasing member comprising an elastic member and configured to retract said detection head away from said support and towards said carrier;
a belt connecting between said detection head and said counterweight;
at least two rollers guiding said belt;
wherein said sensor includes a cord connected between said at least two rollers, and
at least one sensor responsive to a malfunction of said belt to trigger said restrictor, where said sensor includes a cord connected between said at least two rollers and measures a change in tension in said cord in response to an uncoordinated rotation of said at least two rollers.

20. The system of claim 19, wherein said malfunction includes a loss of tension in said belt.

21. The tomographic system of claim 19, wherein said unbalanced movement includes one or more of:
movement of said detection head faster than a limit;
change in tension in said belt; and
change in tension in said cord.

22. The system of claim 19, wherein said at least two rollers are biased to rotate in opposite directions, reduction in tension of said belt thereby increasing tension on said cord.

23. The system of claim 19, wherein said restrictor includes a brake configured to inhibit movement of said detector towards said support.

24. The system of claim 19, comprising a brake including an actuator configured to activate the brake, said system comprising:
a controller receiving a signal from said at least one sensor, said controller including circuitry configured to generate a control signal for control of said brake, based on said signal.

25. The system of claim 24, wherein said sensor is configured to measure and said controller is configured to generate a control signal based on one or more of:
tension on one or more of said cord and said belt; and
speed of movement of said detector head.

26. The tomographic system of claim 19:
wherein said at least one detector head has a field of view including a plurality of directions;
wherein said system comprises:
a shield positioned between said at least one detector head and said support, said shield configured to attenuate a signal detected by said detector uniformly over said field of view; and
a force sensor detecting a force on said shield, said force sensor positioned outside said field of view.

27. The tomographic system of claim 19, comprising:
at least one detector head having a field of view including a plurality of directions; and
a capacitance detector positioned between said at least one detector head and said support, said capacitance detector configured to attenuate a signal detected by said detector uniformly over said field of view.

28. The tomographic system of claim 19, wherein said at least one detector head and said counter weight are connected to move in opposite directions in a coordinated manner; and
wherein said unbalanced movement includes uncoordinated movement of the counterweight and detector head.

29. The tomographic system of claim 19, wherein said sensor comprises an encoder.

30. The tomographic system of claim 29, wherein said encoder is used to limit position and/or movement of said detection head.

31. The tomographic system of claim 30, wherein a signal from said encoder provides an input to a watchdog to restrict movement of said detector head.

* * * * *